US009469858B2

(12) United States Patent
Atkinson et al.

(10) Patent No.: US 9,469,858 B2
(45) Date of Patent: *Oct. 18, 2016

(54) SPORULATION-DEFICIENT THERMOPHILIC MICROORGANISMS FOR THE PRODUCTION OF ETHANOL

(71) Applicant: TMO RENEWABLES LIMITED, Guildford, Surrey (GB)

(72) Inventors: Anthony Atkinson, Guildford (GB); Kirstin Eley, Guildford (GB); Roger Cripps, Guildford (GB)

(73) Assignee: TMO RENEWABLES LIMITED (GB)

( * ) Notice: Subject to any disclaimer, the term of this patent is extended or adjusted under 35 U.S.C. 154(b) by 395 days.

This patent is subject to a terminal disclaimer.

(21) Appl. No.: 13/777,120

(22) Filed: Feb. 26, 2013

(65) Prior Publication Data

US 2014/0080190 A1 Mar. 20, 2014

Related U.S. Application Data

(63) Continuation of application No. 13/127,927, filed as application No. PCT/GB2009/051487 on Nov. 5, 2009, now Pat. No. 8,486,687.

(30) Foreign Application Priority Data

Nov. 5, 2008 (GB) .................. 0820262.4

(51) Int. Cl.
| | |
|---|---|
| C12N 1/20 | (2006.01) |
| C12Q 1/68 | (2006.01) |
| C12N 15/00 | (2006.01) |
| C12N 9/04 | (2006.01) |
| C12N 9/10 | (2006.01) |
| C12P 7/06 | (2006.01) |
| C07H 21/04 | (2006.01) |
| C07K 1/00 | (2006.01) |
| C07K 14/32 | (2006.01) |
| C12R 1/01 | (2006.01) |

(52) U.S. Cl.
CPC .............. *C12P 7/065* (2013.01); *C07K 14/32* (2013.01); *C12N 1/20* (2013.01); *C12N 9/0006* (2013.01); *C12R 1/01* (2013.01); *Y02E 50/17* (2013.01)

(58) Field of Classification Search
CPC .... C12N 15/00; C12N 15/75; C12N 9/0006; C12N 9/1029; C12P 7/065; C07K 14/32
See application file for complete search history.

(56) References Cited

U.S. PATENT DOCUMENTS

| | | | |
|---|---|---|---|
| 5,238,833 A | 8/1993 | Sanders et al. | |
| 5,589,369 A | 12/1996 | Seidman et al. | |
| 6,664,076 B2 | 12/2003 | Green et al. | |
| 7,691,620 B2 | 4/2010 | Green et al. | |
| 8,021,865 B2 | 9/2011 | Atkinson et al. | |
| 2002/0034816 A1 | 3/2002 | Green et al. | |
| 2008/0305536 A1 | 12/2008 | Atkinson et al. | |
| 2009/0042265 A1 | 2/2009 | Atkinson et al. | |
| 2009/0197314 A1 | 8/2009 | Atkinson et al. | |
| 2010/0173373 A1 | 7/2010 | Atkinson et al. | |
| 2011/0318802 A1 | 12/2011 | Atkinson et al. | |

FOREIGN PATENT DOCUMENTS

| | | |
|---|---|---|
| EP | 0124076 A2 | 11/1984 |
| EP | 0351717 A2 | 1/1990 |
| EP | 0 937 774 A1 | 8/1999 |
| FR | 2 477 572 A1 | 9/1981 |
| GB | 2 074 188 A | 8/1981 |
| GB | 2171703 A | 9/1986 |
| JP | 2005-261239 A | 9/2005 |
| WO | WO 98/45425 A1 | 10/1998 |
| WO | WO 88/09379 A2 | 12/1998 |
| WO | WO 01/49865 A1 | 7/2001 |
| WO | WO 01/83784 A2 | 11/2001 |
| WO | WO 02/29030 A3 | 4/2002 |
| WO | WO 2006/117536 A1 | 11/2006 |
| WO | WO 2006/131734 A1 | 12/2006 |
| WO | WO 2007/039753 A1 | 4/2007 |
| WO | WO 2008/038019 A3 | 4/2008 |
| WO | WO 2009/022158 A1 | 2/2009 |
| WO | WO 2010/052499 | 5/2010 |

OTHER PUBLICATIONS

NCBI Database—Geobacillus. Retrieved from the internet on Mar. 22, 2012 via http://www.ncbi.nlm.nih.gov/Taxonomy/Browser/wwwtax.cgi?id=129337.*
UnitProt Database—Geobacillus Lactate Dehydrogenase. Retrived from the internet on Mar. 22, 2012 via http://www.uniprot.org/uniprot/?query=geobacillus++lactate+dehydrogenase&sort=score.*
UnitProt Database—Geobacillus spo0A. Retrived from the internet on Mar. 22, 2012 via http://www.uniprot.org/uniprot/?query=geobacillus+spo0a&sort=score.*
Lewis et al. Domain swapping in the sporulation response regulator Spo0A Mol Biol. Mar. 31, 2000;297(3):757-70.*
Fong, J. C. N. et al. "Isolation and characterization of two novel ethanol-tolerant facultative-anaerobic thermophilic bacteria strains from waste compost" *Extremophiles*, Mar. 2006, 10:363-372.
Kuisiene, N. et al. "Phylogenetic, Inter, and Intraspecific Sequence Analysis of *spo0A* Gene of the Genus *Geobacillus*" *Curr Microbiol*, Feb. 2009, 58:547-553.
Lee, D. H. et al. "Ethanol Fermentation of Corn Starch by a Recombinant *Saccharomyces cerevisiae* Having Glucaomylase and α-Amylase Activities" *J. Food Sci. Nutr.*, 2001, 6(4):206-210.
Molle, V. et al. "The Spo0A regulon of *Bacillus subtilis*" *Molecular Microbiology*, 2003, 50(5):1683-1701.
Payton, M. A. "Production of ethanol by thermophilic bacteria" *Trends in Biotechnology*, 1984, 2(6):153-158.
Stephenson, K. et al. "Molecular insights into the initiation of sporulation in Gram-positive bacteria: new technologies for an old phenomenon" *FEMS Microbiology Reviews*, 2005, 29:281-301.

(Continued)

*Primary Examiner* — Yong Pak
(74) *Attorney, Agent, or Firm* — Saliwanchik, Lloyd & Eisenschenk

(57) ABSTRACT

A thermophilic microorganism comprising a modification that prevents sporulation, wherein the modification inactivates the native spo0A gene.

19 Claims, 8 Drawing Sheets

(56) References Cited

OTHER PUBLICATIONS

De Graef, M.R. et al. "The Steady-State Internal Redox State (NADH/NAD) Reflects the External Redox State and Is Correlated with Catabolic Adaptation in *Escherichia coli*" *J. Bacteriol.*, Apr. 1999, 181(8):2351-2357.
Lapierre, L. et al. "D-Lactate Dehydrogenase Gene (IdhD) Inactivation and Resulting Metabolic Effects in the Lactobacillus johnsonii Strains La1 and N312" *Appl. Environ. Microbiol.*, Sep. 1999, 65(9):4002-4007.
Nakajima, R. et al. "Nucleotide Sequence of the Bacillus stearothermophilus α-Amylase Gene" *J. Bacteriol.*, Jul. 1985, 163(1):401-406.
Office Action dated Sep. 23, 2011 in U.S. Appl. No. 12/376,826, filed May 22, 2009.
Office Action dated Oct. 14, 2011 in U.S. Appl. No. 13/191,056, filed Jul. 26, 2011.
Barstow, D.A. et al. "Cloning, expression and complete nucleotide sequence of the *Bacillus stearothermophilus* L-lactate dehydrogenase gene" Gene, 1986, 46:47-55, abstract.
Biswas, I. et al. "High-Efficiency Gene Inactivation and Replacement System for Gram-Positive Bacteria," Journal of Bacteriology, Jun. 1, 1993, pp. 175(11):3628-3635, Washington, DC, US, XP000563688.
Breuer, M. et al. "High-throughput assay of (R)-phenylacetylcarbinol synthesized by pyruvate decarboxylase" Anal Bioanal Chem, 2002, 374:1069-1073.
Carlsson, J. et al. "Pyruvate Dehydrogenase Activity in Streptococcus mutans" Infection and Immunity, 1985, 49(3):674-678.
Database WPI Week 200567, Thomson Scientific, AN 2005-653380, XP002487167 & JP2005-261239A, Sep. 29, 2005.
Desai, S.G. et al. "Cloning of L-lactate dehydrogenase and elimination of lactic acid production via gene knockout in Thermoanaerobacterium saccharolyticum JW/SL-YS485," Applied Microbiology and Biotechnology, Oct. 2004, 65(5):600-605, XP002393736.
Fortina, M.G. et al. "Reclassification of Saccharococcus caldoxylosilyticus as Geobacillus caldoxylosilyticus (Ahmad et al. 2000) comb nov" International Journal of Systematic and Evolutionary Microbiology, 2001, 51:2063-2071.
Gao, H. et al. "The E1β and E2 Subunits of the Bacillus subtilis Pyruvate Dehydrogenase Complex Are Involved in Regulation of Sporulation" Journal of Bacteriology, May 2002, 184(10):2780-2788.
Geobacillus thermoglucosidasius. NCBI Databases, pp. 1-3, printed from the internet on Oct. 29, 2010.
Germain, P. et al. "Ethanol production by anaerobic thermophilic bacteria: regulation of lactate dehydrogenase activity in Clostridium thermohydrosulfuricum" Appl Microbiol Biotechnol, 1986, 24:300-305.
Hartley, B.S. et al. (May 1983) "Development and Economics of a Novel Thermophilic Ethanol Fermentation" Presentations from Biotech '83 London, May 4-6, 1983 First World Conference, Biotech, Northwood, Online Conf. LTD, GB, pp. 895-905.
Hollmann, R. et al. "Pyruvate formation and suppression in recombinant Bacillus megaterium cultivation" Journal of Biotechnology, 2004, 111:89-96.
Jimenez, J. et al."Selection of Ethanol-Tolerant Yeast Hybrids in pH-Regulated Continuous Culture" Applied and Environmental Microbiology, Apr. 1988, 54(4):917-922.
Larsen, L. et al. "*Thermoanaerobacter mathranii* sp. Nov., an ethanol-producing, extremely thermophilic anaerobic bacterium from a hot spring in Iceland" Arch Microbiol, 1997, 168:114-119.
Lessard, I.A.D. et al. "Expression in *Escherichia coli* of Genes Encoding the E1α and E1β Subunits of the Pyruvate Dehydrogenase Complex of Bacillus stearothermophilis and Assembly of a Functional E1 Component (α1β2) in Vitro" The Journal of Biological Chemistry, 1994, 269(14):10378-10383.
Lynd, L.R. et al. "Thermophilic Ethanol Production: Investigation of Ethanol Yield and Tolerance in Continuous Culture" Applied Biochemistry and Biotechnology, 1991, 28/29:549-570.
Neveling, U. et al. "Gene and subunit organization of bacterial pyruvate dehydrogenase complexes" Biochemica et Biophysica Acta, 1998, 1385:367-372.
Nichols, N.N. et al. "Engineering lactic acid bacteria with pyruvate decarboxylase and alcohol dehydrogenase genes for ethanol production from Zymomonas mobilis" J Ind Microbiol Biotechnol, 2003, 30:315-321.
Niu, X.D. et al. "Cloning and nucleotide sequence of the gene for dihydrolipoamide acetyltransferase from *Saccharomyces cerevisiae*" Proc. Natl. Acad. Sci. USA, Oct. 1988, 85:7546-7550.
San Martin, R. et al. "Development of a synthetic medium for continuous anaerobic growth and ethanol production with a lactate dehydrogenase mutant of Bacillus stearothermophilus," Journal of General Microbiology, Feb. 3, 1992, 138:987-996, Great Britain.
San Martin, R. et al. "Pathways of ethanol production from sucrose by a mutant thermophilic Bacillus in continuous culture," Journal of General Microbiology, Jan. 5, 1993, 139:1033-1040, Great Britain.
Schütz, A. et al. "Crystal structure of thiamindiphosphate-dependent indolepyruvate decarboxylase from Enterobacter cloacae, an enzyme involved in the biosynthesis of the plant hormone indole-3-acetic acid" Eur. J. Biochem., 2003, 270:2312-2321.
Schütz, A. et al. "Studies on structure-function relationships of indolepyruvate decarboxylase from Enterobacter cloacae, a key enzyme of the indole acetic acid pathway" Eur. J. Biochem., 2003, 270:2322-2331.
Siegert, P. et al. "Exchanging the substrate specificities of pyruvate decarboxylase from Zymomonas mobilis and benzoylformate decarboxylase from Pseudomonas putida" Protein Engineering, Design & Selection, 2005, 18(7):345-357.
Tomar, A. et al. "The effect of acetate pathway mutations on the production of pyruvate in *Escherichia coli*" Appl Microbiol Biotechnol, 2003, 62:76-82.
Wendisch, V.F. et al. "Metabolic engineering of *Escherichia coli* and Corynebacterium glutamicum for biotechnological production of organic acids and amino acids" Current Opinion in Microbiology, 2006, 9:268-274.
Witzmann, S. et al. "The pyruvate dehydrogenase complex from the thermophilic organisms: thermal stability and re-association from the enzyme components" Biochemica et Biophysica Acta, 1998, 13885:341-352.
Yomano, L.P. et al. "Isolation and characterization of ethanol-tolerant mutants of *Escherichia coli* KO11 for fuel ethanol production" Journal of Industrial Microbiology & Biotechnology, Feb. 1998, 20(2):132-138.
Office Action dated May 5, 2010 in U.S. Appl. No. 11/915,930, filed Sep. 29, 2008.
Office Action dated Nov. 15, 2010 in U.S. Appl. No. 11/915,930, filed Sep. 29, 2008.
Office Action dated Nov. 17, 2009 in U.S. Appl. No. 11/913,480, filed Apr. 17, 2008.
Office Action dated Jun. 25, 2010 in U.S. Appl. No. 11/913,480, filed Apr. 17, 2008.
Office Action dated Jun. 16, 2011 in U.S. Appl. No. 12/066,526, filed Jun. 29, 2008.
Office Action dated Feb. 18, 2011 in U.S. Appl. No. 12/066,526, filed Jun. 29, 2008.
Office Action dated Mar. 7, 2011 in U.S. Appl. No. 12/376,826, filed May 22, 2009.
Rowe-Magnus et al. "Identification of a second region of the Spo0A response regulator of Bacillus subtilis required for transcription activation" *Journal of Bacteriology*, 2000, 182(15):4352-5.
Lewis et al., "Domain swapping in the sporulation response regulator Spo0A" *Journal of Molecular Biology*, 2000, 297(3):757-70.
UnitProt Database—Geobacillus Lactate Dehydrogenase. Retrieved from internet on Mar. 22, 2012 via http://www.uniprot.org/uniprot/?query=geobacillus++lactate+dehydrogenas&sort=score.
UnitProt Database—Geobacillus spo0A. Retrieved from the internet on Mar. 22, 2012 via http://www.uniprotorg/uniprot/?query=geobacillus+spo)a&sort=score . . . .
Kuisiene, N. et al., "Phylogenetic, Inter, and Intraspecific Sequence Analysis of spo0A Gene of the Genus *Geobacillus*" *Curr. Microbiol.*, 2009, vol. 58, pp. 547-553.
Studholme, D.J., "Some (bacilli) like it hot: genomics of *Geobacillus* species" *Microbial Biotechnology*, 2015, vol. 8, pp. 40-48.

* cited by examiner

TTGGGAGTAAGGGGGAAGGTTTTCTTGAAAATTAAAGTATGTATTGCGGACGATAACCGT
GAGTTAGTGAATTTGCTCGAAGAATATATTTCCAGCCAAAGCGACATGGAAGTGATCGGG
ACTGCTTATAATGGCCAAGATTGCTTATATATGCTCGAGGAAAAACAACCGGATGTGTTA
TTGTTAGACATTATTATGCCTCATTTAGATGGATTGGCCGTATTGGAAAAAATTCGTGCG
AAGCGGGAAAAACAACCGAGCGTGATCATGCTGACAGCATTTGGCCAAGAAGATGTAACG
AAAAAAGCGGTTGAACTTGGCGCCTCTTATTTTATTTTAAAACCGTTTGACATGGAAAAT
TTAGTGTATCATATCCGCCAAGTGCATGGAAAAACGGCACCAATGGTGAAAAAAGCGGCG
TCTGCCTACCAAACGCGGGATAACAGGCCGAAAAATCTGGACGCAAGCATTACGAGCATC
ATTCATGAAATCGGCGTTCCGGCGCATATTAAAGGATATTTATATTTACGTGAAGCGATC
GCCATGGTGTATAACGATATTGAATTGCTCGGCGCAATTACGAAAGTGCTTTACCCGGAC
ATTGCCAAAAAATATAACACAACGGCCAGCCGTGTCGAGCGGGCGATCCGCCATGCGATT
GAAGTCGCTTGGAGCCGCGGCAATCTCGAATCGATTTCTTCCTTATTCGGCTACACCGTC
AGCGTGTCGAAAGCCAAACCGACAAACAGCGAATTCATCGCGATGGTCGCCGATAAGTTA
AGATTAGAGCATAAAGCTTCTTAA

FIGURE 1

MGVRGKVFLKIKVCIADDNRELVNLLEEYISSQSDMEVIGTAYNGQDCLYMLEEKQPDVL
LLDIIMPHLDGLAVLEKIRAKREKQPSVIMLTAFGQEDVTKKAVELGASYFILKPFDMEN
LVYHIRQVHGKTAPMVKKAASAYQTRDNRPKNLDASITSIIHEIGVPAHIKGYLYLREAI
AMVYNDIELLGAITKVLYPDIAKKYNTTASRVERAIRHAIEVAWSRGNLESISSLFGYTV
SVSKAKPTNSEFIAMVADKLRLEHKAS

FIGURE 2

Lane 1: #7 (in-frame)
Lane 2: #9 (out-of-frame)
Lane 3: #13 (out-of-frame)
Lane 4: #16 (wild-type)
Lane 5: TM242

SEQUENCE LISTING

<160> NUMBER OF SEQ ID NOS: 4

<210> SEQ ID NO 1
<211> LENGTH: 804
<212> TYPE: DNA
<213> ORGANISM: Geobacillus thermoglucosidasius

<400> SEQUENCE: 1

```
ttgggagtaa gggggaaggt tttcttgaaa attaaagtat gtattgcgga cgataaccgt      60
gagttagtga atttgctcga agaatatatt tccagccaaa gcgacatgga agtgatcggg     120
actgcttata atggccaaga ttgcttatat atgctcgagg aaaaacaacc ggatgtgtta     180
ttgttagaca ttattatgcc tcatttagat ggattggccg tattggaaaa aattcgtgcg     240
aagcgggaaa aacaaccgag cgtgatcatg ctgacagcat ttggccaaga agatgtaacg     300
aaaaaagcgg ttgaacttgg cgcctcttat tttattttaa aaccgtttga catggaaaat     360
```

```
ttagtgtatc atatccgcca agtgcatgga aaaacggcac caatggtgaa aaagcggcg    420 tctgcctacc aaacgcggga taacaggccg aaaaatctgg acgcaagcat tacgagcatc   480
attcatgaaa tcggcgttcc ggcgcatatt aaaggatatt tatatttacg tgaagcgatc   540
gccatggtgt ataacgatat tgaattgctc ggcgcaatta cgaaagtgct ttacccggac   600
attgccaaaa aatataacac aacggccagc cgtgtcgagc gggcgatccg ccatgcgatt   660
gaagtcgctt ggagccgcgg caatctcgaa tcgatttctt ccttattcgg ctacaccgtc   720
agcgtgtcga aagccaaacc gacaaacagc gaattcatcg cgatggtcgc cgataagtta   780
agattagagc ataaagcttc ttaa                                          804
```

```
<210> SEQ ID NO 2
<211> LENGTH: 267
<212> TYPE: PRT
<213> ORGANISM: Geobacillus thermoglucosidasius

<400> SEQUENCE: 2

Met Gly Val Arg Gly Lys Val Phe Leu Lys Ile Lys Val Cys Ile Ala
1               5                   10                  15

Asp Asp Asn Arg Glu Leu Val Asn Leu Leu Glu Glu Tyr Ile Ser Ser
            20                  25                  30

Gln Ser Asp Met Glu Val Ile Gly Thr Ala Tyr Asn Gly Gln Asp Cys
        35                  40                  45

Leu Tyr Met Leu Glu Glu Lys Gln Pro Asp Val Leu Leu Asp Ile
    50                  55                  60

Ile Met Pro His Leu Asp Gly Leu Ala Val Leu Glu Lys Ile Arg Ala
65                  70                  75                  80

Lys Arg Glu Lys Gln Pro Ser Val Ile Met Leu Thr Ala Phe Gly Gln
                85                  90                  95

Glu Asp Val Thr Lys Lys Ala Val Glu Leu Gly Ala Ser Tyr Phe Ile
            100                 105                 110

Leu Lys Pro Phe Asp Met Glu Asn Leu Val Tyr His Ile Arg Gln Val
        115                 120                 125

His Gly Lys Thr Ala Pro Met Val Lys Lys Ala Ser Ala Tyr Gln
    130                 135                 140

Thr Arg Asp Asn Arg Pro Lys Asn Leu Asp Ala Ser Ile Thr Ser Ile
145                 150                 155                 160

Ile His Glu Ile Gly Val Pro Ala His Ile Lys Gly Tyr Leu Tyr Leu
                165                 170                 175

Arg Glu Ala Ile Ala Met Val Tyr Asn Asp Ile Glu Leu Leu Gly Ala
            180                 185                 190

Ile Thr Lys Val Leu Tyr Pro Asp Ile Ala Lys Lys Tyr Asn Thr Thr
        195                 200                 205

Ala Ser Arg Val Glu Arg Ala Ile Arg His Ala Ile Glu Val Ala Trp
    210                 215                 220

Ser Arg Gly Asn Leu Glu Ser Ile Ser Ser Leu Phe Gly Tyr Thr Val
225                 230                 235                 240

Ser Val Ser Lys Ala Lys Pro Thr Asn Ser Glu Phe Ile Ala Met Val
                245                 250                 255

Ala Asp Lys Leu Arg Leu Glu His Lys Ala Ser
            260                 265

<210> SEQ ID NO 3
<211> LENGTH: 5082
<212> TYPE: DNA
```

<213> ORGANISM: Geobacillus thermoglucosidasius

<400> SEQUENCE: 3

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatatg cggtgtgaaa taccgcacag atgcgtaagg agaaaatacc gcatcaggcg     240
taaccaacat gattaacaat tattagaggt catcgttcaa aatggtatgc gttttgacac     300
atccactata tatccgtgtc gttctgtcca ctcctgaatc ccattccaga aattctctag     360
cgattccaga agtttctcag agtcggaaag ttgaccagac attacgaact ggcacagatg     420
gtcataacct gaaggaagat ctgattgctt aactgcttca gttaagaccg aagcgctcgt     480
cgtataacag atgcgatgat gcagaccaat caacatggca cctgccattg ctacctgtac     540
agtcaaggat ggtagaaatg ttgtcggtcc ttgcacacga atattacgcc atttgcctgc     600
atattcaaac agctcttcta cgataagggc acaaatcgca tcgtggaacg tttgggcttc     660
taccgattta gcagtttgat acactttctc taagtatcca cctgaatcat aaatcggcaa     720
aatagagaaa aattgaccat gtgtaagcgg ccaatctgat tccacctgag atgcataatc     780
tagtagaatc tcttcgctat caaaattcac ttccaccttc cactcaccgg ttgtccattc     840
atggctgaac tctgcttcct ctgttgacat gacacacatc atctcaatat ccgaataggg     900
cccatcagtc tgacgaccaa gagagccata acaccaata gccttaacat catccccata     960
tttatccaat attcgttcct taatttcatg aacaatcttc attctttctt ctctagtcat    1020
tattattggt ccattcacta ttctcattcc cttttcagat aattttagat ttgcttttct    1080
aaataagaat atttggagag caccgttctt attcagctat taataactcg tcttcctaag    1140
catccttcaa tccttttaat aacaattata gcatctaatc ttcaacaaac tggcccgttt    1200
gttgaactac tctttaataa aataattttt ccgttcccaa ttccacattg caataataga    1260
aaatccatct tcatcggctt tttcgtcatc atctgtatga atcaaatcgc cttcttctgt    1320
gtcatcaagg tttaattttt tatgtatttc ttttaacaaa ccaccatagg agattaacct    1380
tttacggtgt aaaccttcct ccaaatcaga caaacgtttc aaattctttt cttcatcatc    1440
ggtcataaaa tccgtatcct ttacaggata ttttgcagtt tcgtcaattg ccgattgtat    1500
atccgattta tatttatttt tcggtcgaat catttgaact tttacatttg gatcatagtc    1560
taatttcatt gccttttttcc aaaattgaat ccattgtttt tgattcacgt agttttctgt    1620
attcttaaaa taagttggtt ccacacatac caatacatgc atgtgctgat tataagaatt    1680
atctttatta tttattgtca cttccgttgc acgcataaaa ccaacaagat ttttattaat    1740
ttttttatat tgcatcattc ggcgaaatcc ttgagccata tctgacaaac tcttatttaa    1800
ttcttcgcca tcataaacat ttttaactgt taatgtgaga aacaaccaac gaactgttgg    1860
cttttgttta ataacttcag caacaacctt ttgtgactga atgccatgtt tcattgctct    1920
cctccagttg cacattggac aaagcctgga tttacaaaac cacactcgat acaactttct    1980
ttcgcctgtt tcacgatttt gtttatactc taatatttca gcacaatctt ttactctttc    2040
agccttttta aattcaagaa tatgcagaag ttcaaagtaa tcaacattag cgattttctt    2100
ttctctccat ggtctcactt ttccactttt tgtcttgtcc actaaaaccc ttgattttttc    2160
atctgaataa atgctactat taggacacat aatattaaaa gaaaccccca tctatttagt    2220
tatttgttta gtcacttata actttaacag atggggtttt tctgtgcaac caattttaag    2280
```

```
ggttttcaat actttaaaac acatacatac caacacttca acgcacctt cagcaactaa      2340 aataaaaatg acgttatttc tatatgtatc aagataagaa agaacaagtt caaaaccatc      2400
aaaaaaagac accttttcag gtgctttttt tattttataa actcattccc tgatctcgac      2460
ttcgttcttt ttttacctct cggttatgag ttagttcaaa ttcgttcttt ttaggttcta      2520
aatcgtgttt ttcttggaat tgtgctgttt tatcctttac cttgtctaca aaccccttaa      2580
aaacgttttt aaaggctttt aagccgtctg tacgttcctt aaggaattaa ttcgccattc      2640
gccattcagg ctgcgcaact gttgggaagg gcgatcggtg cgggcctctt cgctattacg      2700
ccagctggcg aaaggggat gtgctgcaag gcgattaagt tgggtaacgc cagggttttc      2760
ccagtcacga cgttgtaaaa cgacggccag tgaattcgag ctcggtaccc ggggatcctc      2820
tagagtcgac ctgcaggcat gcaagcttgg cgtaatcatg gtcatagctg tttcctgtgt      2880
gaaattgtta tccgctcaca attccacaca acatacgagc cggaagcata aagtgtaaag      2940
cctggggtgc ctaatgagtg agctaactca cattaattgc gttgcgctca ctgcccgctt      3000
tccagtcggg aaacctgtcg tgccagctgc attaatgaat cggccaacgc gcggggagag      3060
gcggtttgcg tattgggcgc tcttccgctt cctcgctcac tgactcgctg cgctcggtcg      3120
ttcggctgcg gcgagcggta tcagctcact caaaggcggt aatacggtta ccacagaat      3180 caggggataa cgcaggaaag aacatgtgag caaaaggcca gcaaaaggcc aggaaccgta      3240
aaaaggccgc gttgctggcg ttttccata ggctccgccc ccctgacgag catcacaaaa      3300
atcgacgctc aagtcagagg tggcgaaacc cgacaggact ataaagatac caggcgtttc      3360
cccctggaag ctccctcgtg cgctctcctg ttccgaccct gccgcttacc ggatacctgt      3420
ccgcctttct cccttcggga agcgtggcgc tttctcatag ctcacgctgt aggtatctca      3480
gttcggtgta ggtcgttcgc tccaagctgg gctgtgtgca cgaaccccc gttcagcccg      3540 accgctgcgc cttatccggt aactatcgtc ttgagtccaa cccggtaaga cacgacttat      3600
cgccactggc agcagccact ggtaacagga ttagcagagc gaggtatgta ggcggtgcta      3660
cagagttctt gaagtggtgg cctaactacg gctacactag aagaacagta tttggtatct      3720
gcgctctgct gaagccagtt accttcggaa aaagagttgg tagctcttga tccggcaaac      3780
aaaccaccgc tggtagcggt ggttttttg tttgcaagca gcagattacg cgcagaaaaa      3840
aaggatctca agaagatcct ttgatctttt ctacggggtc tgacgctcag tggaacgaaa      3900
actcacgtta agggattttg gtcatgagat tatcaaaaag gatcttcacc tagatccttt      3960
taaattaaaa atgaagtttt aaatcaatct aaagtatata tgagtaaact tggtctgaca      4020
gttaccaatg cttaatcagt gaggcaccta tctcagcgat ctgtctattt cgttcatcca      4080
tagttgcctg actccccgtc gtgtagataa ctacgatacg ggagggctta ccatctggcc      4140
ccagtgctgc aatgataccg cgagacccac gctcaccggc tccagattta tcagcaataa      4200
accagccagc cggaagggcc gagcgcagaa gtggtcctgc aacttatcc gcctccatcc      4260 agtctattaa ttgttgccgg gaagctagag taagtagttc gccagttaat agtttgcgca      4320
acgttgttgc cattgctaca ggcatcgtgg tgtcacgctc gtcgtttggt atggcttcat      4380
tcagctccgg ttcccaacga tcaaggcgag ttacatgatc ccccatgttg tgcaaaaaag      4440
cggttagctc cttcggtcct ccgatcgttg tcagaagtaa gttggccgca gtgttatcac      4500
tcatggttat ggcagcactg cataattctc ttactgtcat gccatccgta agatgctttt      4560
ctgtgactgg tgagtactca accaagtcat tctgagaata gtgtatgcgg cgaccgagtt      4620
```

| | |
|---|---|
| gctcttgccc ggcgtcaata cgggataata ccgcgccaca tagcagaact ttaaaagtgc | 4680 |
| tcatcattgg aaaacgttct tcggggcgaa aactctcaag gatcttaccg ctgttgagat | 4740 |
| ccagttcgat gtaacccact cgtgcaccca actgatcttc agcatctttt actttcacca | 4800 |
| gcgtttctgg gtgagcaaaa acaggaaggc aaaatgccgc aaaaaaggga ataagggcga | 4860 |
| cacggaaatg ttgaatactc atactcttcc tttttcaata ttattgaagc atttatcagg | 4920 |
| gttattgtct catgagcgga tacatatttg aatgtattta gaaaaataaa caaatagggg | 4980 |
| ttccgcgcac atttccccga aaagtgccac ctgacgtcta agaaaccatt attatcatga | 5040 |
| cattaaccta taaaaatagg cgtatcacga ggccctttcg tc | 5082 |

<210> SEQ ID NO 4
<211> LENGTH: 15044
<212> TYPE: DNA
<213> ORGANISM: Geobacillus thermoglucosidasius

<400> SEQUENCE: 4

| | |
|---|---|
| aaaatcaatc tcttttttcca agtttgtttt tttaaattta gctgtctcaa tatgtttacg | 60 |
| gtcagagcca cgttcaccac gcttcaactc aaaaccctgt ttttagttag agaaaaaggt | 120 |
| ttcaaacaaa aaatttaaat cgacagagtt atacaaatgc cagtctcggt gcaagtggtg | 180 |
| cgaagttgag ttttgggaca ttttttcatat gctcggggaa tttatcttgt agccataaca | 240 |
| gttcttgacg attaaacaca ttttttcctt gcagttttcc atcacgcata ggcacaacac | 300 |
| aaaaagtata cgagccccctt aaatagaaca tcggtattgt caagaactgc taatttgtgt | 360 |
| aaaaaaggaa cgtcaaaagg tagtgcgtat ccgtgttgtg ctaaatgcat gtgaggggtt | 420 |
| tgctcatcat tatgaactgt tgcataagca atattttgct tgccatatcg ttcggaaaat | 480 |
| aatttataac tttcctcaaa gatttacgta cactccccaa acgagtagta atacttgaca | 540 |
| acgtattcgt tataaaacga acggtatagc aagcctttta ttaaatattg aaaggagttt | 600 |
| aaaatcgtttt tgttctcctg gatccagttg ctcaaaaaaa tctcggtcag atgttactag | 660 |
| caactcatttt acaagaacag catctttcct cgttttttctt tttagcaaaa acaagaggac | 720 |
| ctaggtcaac gagttttttt agagccagtc tacaatgatc gttgagtaaa tgttcttgtc | 780 |
| gtagaaagga gcaaaaagaa gtacctgttt tttgtgattc aataatttct ttgacacgtt | 840 |
| cgttgtaatc aatattttta tcattttttca aatcataatt ttcacgtgtt cgctcatggt | 900 |
| catggacaaa aaacactaag ttattaaaga aactgtgcaa gcaacattag ttataaaaat | 960 |
| agtaaaaagt ttagtattaa aagtgcacaa gcgagtacca caatatcatc attcgttcta | 1020 |
| cttttttcgct ctctttgatt atgaaattgc atgcctttta gtccagctga tttcactttt | 1080 |
| tgcattctac aaactgcata gttatagtag taagcaagat gaaaaagcga gagaaactaa | 1140 |
| tactttaacg tacggaaaat caggtcgact aaagtgaaaa acgtaagatg tttgacgtat | 1200 |
| actcatatgt aaatcgctcc tttttaggtg gcacaaatgt gaggcatttt cgctcttttcc | 1260 |
| ggcaaccact tccaagtaaa gtaacacaca ctatacttta tgagtataca tttagcgagg | 1320 |
| aaaaatccac cgtgtttaca ctccgtaaaa gcgagaaagg ccgttggtga aggttcattt | 1380 |
| catattgtgt gatatgaaat tattcataaa gtgtgtgctc tgcgaggctg tcggcagtgc | 1440 |
| cgaccaaaac cataaaacct ttaagacctt tcttttttt acgagaaaaa agaaacaaaa | 1500 |
| ataagtattt cacacacgag acgctccgac agccgtcacg gctggttttg gtattttgga | 1560 |
| aattctggaa agaaaaaaaa tgctcttttt tctttgtttt aaacctgccc tctgccacct | 1620 |
| cagcaaaggg gggttttgct ctcgtgctcg tttaaaaatc agcaagggac aggtagtatt | 1680 |

```
ttttgagaag atcactcaaa tttggacggg agacggtgga gtcgtttccc cccaaaacga    1740
gagcacgagc aaattttag tcgttccctg tccatcataa aaaactcttc tagtgagttt     1800
aaatctccac ctttaaaccc ttgccaattt ttattttgtc cgttttgtct agcttaccga    1860
aagccagact cagcaagaat aaaatttta ttgtctttcg tttagaggtg gaaatttggg     1920
aacggttaaa aataaaacag gcaaaacaga tcgaatggct ttcggtctga gtcgttctta   1980
ttttaaaaat aacagaaagc gttttctagt gtaacggaca aaaccactca aaataaaaaa   2040
gatacaagag aggtctctcg tatctttat tcagcaatcg cgcccgattg ctgaacagat    2100
caaaagatca cattgcctgt tttggtgagt tttattttt ctatgttctc tccagagagc    2160
atagaaaata agtcgttagc gcgggctaac gacttgtcta aataatagaa tttagctttt   2220
ttatttgttg aaaaaagcta atcaaattgt tgtcgggatc aattactgca aagtctcgtt   2280
catcccacca ctgatctttt attattatct aaaatcgaaa aataaacaac ttttttcgat   2340
tagtttaaca acagccctag ttaatgacgt ttcagagcaa gtagggtggt gactagaaaa   2400
aatgatgtat tggggtgcaa aatgcccaaa ggcttaatat gttgatataa ttcatcaatt   2460
ccctctactt caatgcggca actagcagta ccagcaataa ttactacata accccacgtt   2520
ttacgggttt ccgaattata caactatatt aagtagttaa gggagatgaa gttacgccgt   2580
tgatcgtcat ggtcgttatt acgactccgc acctgtacaa accggtgaat cattactacg   2640
agagcgccag ccttcatcac ttgcctccca tagatgaatc cgaacctcat tacacattag   2700
tgctgaggcg tggacatgtt tggccactta gtaatgatgc tctcgcggtc ggaagtagtg   2760
aacggagggt atctacttag gcttggagta atgtgtaatc aactgcgaat ccatcttcat   2820
ggtgaaccaa agtgaaacct agtttatcgc aataaaaacc tatactcttt ttaatatccc   2880
cgactggcaa tgccgggata ttgacgctta ggtagaagta ccacttggtt tcactttgga   2940
tcaaatagcg ttatttttgg atatgagaaa aattataggg gctgaccgtt acggccctat   3000
gactgtaaca ttctcacgca taaaatcccc tttcattttc taatgtaaat ctattacctt   3060
attattaatt caattcgctc ataattaatc ctttttctta ctgacattgt aagagtgcgt   3120
attttagggg aaagtaaaag attacattta gataatggaa taataattaa gttaagcgag   3180
tattaattag gaaaaagaat ttacgcaaaa tggcccgatt taagcacacc ctttattccg   3240
ttaatgcgcc atgacagcca tgataattac taatactagg agaagttaat aaatacgtaa   3300
aatgcgtttt accgggctaa attcgtgtgg gaaataaggc aattacgcgg tactgtcggt   3360
actattaatg attatgatcc tcttcaatta tttatgcatt ccaacatgat taacaattat   3420
tagaggtcat cgttcaaaat ggtatgcgtt ttgacacatc cactatatat ccgtgtcgtt   3480
ctgtccactc ctgaatccca ggttgtacta attgttaata atctccagta gcaagtttta   3540
ccatacgcaa aactgtgtag gtgatatata ggcacagcaa gacaggtgag gacttagggt   3600
ttccagaaat tctctagcga ttccagaagt ttctcagagt cggaaagttg accagacatt   3660
acgaactggc acagatggtc ataacctgaa ggaagatctg aaggtcttta agagatcgct   3720
aaggtcttca aagagtctca gccttttcaac tggtctgtaa tgcttgaccg tgtctaccag   3780
tattggactt ccttctagac attgcttaac tgcttcagtt aagaccgaag cgctcgtcgt   3840
ataacagatg cgatgatgca gaccaatcaa catggcacct gccattgcta cctgtacagt   3900
taacgaattg acgaagtcaa ttctggcttc gcgagcagca tattgtctac gctactacgt   3960
ctggttagtt gtaccgtgga cggtaacgat ggacatgtca caaggatggt agaaatgttg   4020
```

```
tcggtccttg cacacgaata ttacgccatt tgcctgcata ttcaaacagc tcttctacga    4080
taagggcaca aatcgcatcg gttcctacca tctttacaac agccaggaac gtgtgcttat    4140
aatgcggtaa acggacgtat aagtttgtcg agaagatgct attcccgtgt ttagcgtagc    4200
tggaacgttt gggcttctac cgatttagca gtttgataca cttctctaa gtatccacct     4260 gaatcataaa tcggcaaaat agagaaaaat tgaccatgtg accttgcaaa cccgaagatg    4320
gctaaatcgt caaactatgt gaaagagatt cataggtgga cttagtattt agccgtttta    4380
tctcttttta actggtacac taagcggcca atctgattcc acctgagatg cataatctag    4440
tagaatctct tcgctatcaa aattcacttc caccttccac tcaccggttg tccattcatg    4500
attcgccggt tagactaagg tggactctac gtattagatc atcttagaga agcgatagtt    4560
ttaagtgaag gtggaaggtg agtggccaac aggtaagtac gctgaactct gcttcctctg    4620
ttgacatgac acacatcatc tcaatatccg aatagggccc atcagtctga cgaccaagag    4680
agccataaac accaatagcc cgacttgaga cgaaggagac aactgtactg tgtgtagtag    4740
agttataggc ttatcccggg tagtcagact gctggttctc tcggtatttg tggttatcgg    4800
ttaacatcat ccccatattt atccaatatt cgttccttaa tttcatgaac aatcttcatt    4860 cttttcttctc tagtcattat tattggtcca ttcactattc aattgtagta ggggtataaa    4920
taggttataa gcaaggaatt aaagtacttg ttagaagtaa gaaagaagag atcagtaata    4980
ataaccaggt aagtgataag tcattccctt ttcagataat tttagatttg cttttctaaa    5040
taagaatatt tggagagcac cgttcttatt cagctattaa taactcgtct tcctaagcat    5100
agtaagggaa aagtctatta aaatctaaac gaaaagattt attcttataa acctctcgtg    5160
gcaagaataa gtcgataatt attgagcaga aggattcgta ccttcaatcc ttttaataac    5220
aattatagca tctaatcttc aacaaactgg cccgtttgtt gaactactct ttaataaaat    5280 aattttccg ttcccaattc ggaagttagg aaaattattg ttaatatcgt agattagaag     5340
ttgtttgacc gggcaaacaa cttgatgaga aattatttta ttaaaaggc aagggttaag     5400 cacattgcaa taatagaaaa tccatcttca tcggcttttt cgtcatcatc tgtatgaatc    5460
aaatcgcctt cttctgtgtc atcaaggttt aattttttat gtgtaacgtt attatctttt    5520
aggtagaagt agccgaaaaa gcagtagtag acatacttag tttagcggaa gaagacacag    5580
tagttccaaa ttaaaaaata gtatttcttt taacaaacca ccataggaga ttaacctttt    5640
acggtgtaaa ccttcctcca aatcagacaa acgtttcaaa ttcttttctt catcatcggt    5700
cataaagaaa attgtttggt ggtatcctct aattggaaaa tgccacattt ggaaggaggt    5760
ttagtctgtt tgcaaagttt aagaaaagaa gtagtagcca cataaaatcc gtatcccttta  5820 caggatatttt tgcagtttcg tcaattgccg attgtatatc cgatttatat ttatttttcg   5880
gtcgaatcat ttgaactttt gtattttagg cataggaaat gtcctataaa acgtcaaagc    5940
agttaacggc taacatatag gctaaatata aataaaaagc cagcttagta aacttgaaaa    6000
acatttggat catagtctaa tttcattgcc ttttccaaa attgaatcca ttgttttga      6060 ttcacgtagt tttctgtatt cttaaaataa gttggttcca tgtaaaccta gtatcagatt    6120
aaagtaacgg aaaaaggttt taacttaggt aacaaaaact aagtgcatca aaagacataa    6180
gaattttatt caaccaaggt cacataccaa tacatgcatg tgctgattat aagaattatc    6240
tttattattt attgtcactt ccgttgcacg cataaaacca acaagatttt tattaatttt    6300
gtgtatggtt atgtacgtac acgactaata ttccttaatag aaataataaa taacagtgaa   6360
ggcaacgtgc gtattttggt tgttctaaaa ataattaaaa tttatattgc atcattcggc    6420
```

```
gaaatccttg agccatatct gacaaactct tatttaattc ttcgccatca taaacatttt      6480
taactgttaa tgtgagaaac aaatataacg tagtaagccg ctttaggaac tcggtataga      6540
ctgtttgaga ataaattaag aagcggtagt atttgtaaaa attgacaatt acactctttg      6600
aaccaacgaa ctgttggctt ttgtttaata acttcagcaa caaccttttg tgactgaatg      6660
ccatgtttca ttgctctcct ccagttgcac attggacaaa ttggttgctt gacaaccgaa      6720
aacaaattat tgaagtcgtt gttggaaaac actgacttac ggtacaaagt aacgagagga      6780
ggtcaacgtg taacctgttt gcctggattt acaaaccac actcgataca actttctttc       6840
gcctgtttca cgattttgtt tatactctaa tatttcagca caatctttta ctctttcagc      6900
cggacctaaa tgttttggtg tgagctatgt tgaagaaag cggacaaagt gctaaaacaa       6960
atatgagatt ataaagtcgt gttagaaaat gagaaagtcg cttttaaat tcaagaatat       7020 gcagaagttc aaagtaatca acattagcga ttttcttttc tctccatggt ctcacttttc      7080
cactttttgt cttgtccact gaaaaattta agttcttata cgtcttcaag tttcattagt      7140
tgtaatcgct aaaagaaaag agaggtacca gagtgaaaag gtgaaaaaca gaacaggtga      7200 aaaaccttg attttcatc tgaataaatg ctactattag gacacataat attaaaagaa        7260 accccatct atttagttat tgtttagtc acttataact ttttgggaac taaaaagtag        7320 acttattac gatgataatc ctgtgtatta aattttcttt tggggtaga taaatcaata        7380 aacaaatcag tgaatattga ttaacagatg gggttttct gtgcaaccaa ttttaagggt       7440
tttcaatact ttaaaacaca tacataccaa cacttcaacg caccttcag caactaaaat       7500 aattgtctac cccaaaaga cacgttggtt aaaattccca aaagttatga aattttgtgt       7560
atgtatggtt gtgaagttgc gtggaaagtc gttgatttta aaaatgacg ttatttctat       7620 atgtatcaag ataagaaga acaagttcaa aaccatcaaa aaaagacacc ttttcaggtg       7680 cttttttat tttataaact tttttactgc aataaagata tacatagttc tattcttct       7740 tgttcaagtt ttggtagttt ttttctgtgg aaaagtccac gaaaaaata aaatatttga      7800 cattccctga tctcgacttc gttctttttt tacctctcgg ttatgagtta gttcaaattc     7860 gttctttta ggttctaaat cgtgtttttc ttggaattgt gtaagggact agagctgaag       7920
caagaaaaaa atggagagcc aatactcaat caagtttaag caagaaaaat ccaagattta     7980
gcacaaaaag aaccttaaca gctgttttat cctttacctt gtctacaaac cccttaaaaa     8040 cgttttaaa ggcttttaag ccgtctgtac gttccttaag gaattcactg gccgtcgttt      8100
cgacaaaata ggaaatggaa cagatgtttg gggaattttt gcaaaaattt ccgaaaattc    8160
ggcagacatg caaggaattc cttaagtgac cggcagcaaa tacaacgtcg tgactgggaa    8220
aaccctggcg ttacccaact taatcgcctt gcagcacatc ccctttcgc cagctggcgt     8280 aatagcgaag aggcccgcac atgttgcagc actgacccct ttgggaccgc aatgggttga   8340
attagcggaa cgtcgtgtag ggggaaagcg gtcgaccgca ttatcgcttc tccgggcgtg   8400
cgatcgccct tcccaacagt tgcgcagcct gaatggcgaa tggcgcctga tgcggtattt    8460
tctccttacg catctgtgcg gtatttcaca ccgcatatgg gctagcggga agggttgtca   8520
acgcgtcgga cttaccgctt accgcggact acgccataaa agaggaatgc gtagacacgc   8580
cataaagtgt ggcgtatacc tgcactctca gtacaatctg ctctgatgcc gcatagttaa   8640
gccagccccg acaccgcca acacccgctg acgcgccctg acgggcttgt ctgctcccgg    8700
acgtgagagt catgttagac gagactacgg cgtatcaatt cggtcggggc tgtgggcggt    8760
```

```
tgtgggcgac tgcgcgggac tgcccgaaca gacgagggcc catccgctta cagacaagct   8820
gtgaccgtct ccgggagctg catgtgtcag aggttttcac cgtcatcacc gaaacgcgcg   8880
agacgaaagg gcctcgtgat gtaggcgaat gtctgttcga cactggcaga ggccctcgac   8940
gtacacagtc tccaaaagtg gcagtagtgg ctttgcgcgc tctgctttcc cggagcacta   9000
acgcctattt ttataggtta atgtcatgat aataatggtt tcttagacgt caggtggcac   9060
ttttcgggga atgtgcgcg gaaccccta ttgtttattt tgcggataaa aatatccaat     9120
tacagtacta ttattaccaa agaatctgca gtccaccgtg aaaagcccct ttacacgcgc   9180
cttggggata aacaaataaa ttctaaatac attcaaatat gtatccgctc atgagacaat   9240
aaccctgata aatgcttcaa taatattgaa aaggaagag tatgagtatt caacatttcc    9300
aagatttatg taagtttata cataggcgag tactctgtta ttgggactat ttacgaagtt   9360
attataactt tttccttctc atactcataa gttgtaaagg gtgtcgccct tattcccttt   9420
tttgcggcat tttgccttcc tgttttttgct cacccagaaa cgctggtgaa agtaaaagat  9480
gctgaagatc agttgggtgc cacagcggga ataagggaaa aaacgccgta aaacggaagg   9540
acaaaaacga gtgggtcttt gcgaccactt tcattttcta cgacttctag tcaacccacg   9600
acgagtgggt tacatcgaac tggatctcaa cagcggtaag atccttgaga gttttcgccc   9660
cgaagaacgt tttccaatga tgagcacttt taaagttctg tgctcaccca atgtagcttg   9720
acctagagtt gtcgccattc taggaactct caaaagcggg gcttcttgca aaaggttact   9780
actcgtgaaa atttcaagac ctatgtggcg cggtattatc ccgtattgac gccgggcaag   9840
agcaactcgg tcgccgcata cactattctc agaatgactt ggttgagtac tcaccagtca   9900
gatacaccgc gccataatag ggcataactg cggcccgttc tcgttgagcc agcggcgtat   9960
gtgataagag tcttactgaa ccaactcatg agtggtcagt cagaaaagca tcttacggat  10020
ggcatgacag taagagaatt atgcagtgct gccataacca tgagtgataa cactgcggcc  10080
aacttacttc tgacaacgat gtcttttcgt agaatgccta ccgtactgtc attctcttaa  10140
tacgtcacga cggtattggt actcactatt gtgacgccgg ttgaatgaag actgttgcta  10200
cggaggaccg aaggagctaa ccgctttttt gcacaacatg ggggatcatg taactcgcct  10260
tgatcgttgg gaaccggagc tgaatgaagc cataccaaac gcctcctggc ttcctcgatt  10320
ggcgaaaaaa cgtgttgtac cccctagtac attgagcgga actagcaacc cttggcctcg  10380
acttacttcg gtatggtttg gacgagcgtg acaccacgat gcctgtagca atggcaacaa  10440
cgttgcgcaa actattaact ggcgaactac ttactctagc ttcccggcaa caattaatag  10500
ctgctcgcac tgtggtgcta cggacatcgt taccgttgtt gcaacgcgtt tgataattga  10560
ccgcttgatg aatgagatcg aagggccgtt gttaattatc actggatgga gcggataaaa  10620
gttgcaggac cacttctgcg ctcggccctt ccggctggct ggtttattgc tgataaatct  10680
ggagccggtg agcgtgggtc tgacctacct ccgcctattt caacgtcctg gtgaagacgc  10740
gagccgggaa ggccgaccga ccaaataacg actatttaga cctcggccac tcgcacccag  10800
tcgcggtatc attgcagcac tggggccaga tggtaagccc tcccgtatcg tagttatcta  10860
cacgacgggg agtcaggcaa ctatggatga acgaaataga agcgccatag taacgtcgtg  10920
accccggtct accattcggg agggcatagc atcaatagat gtgctgcccc tcagtccgtt  10980
gatacctact tgctttatct cagatcgctg agataggtgc ctcactgatt aagcattggt  11040
aactgtcaga ccaagtttac tcatatatac tttagattga tttaaaactt cattttaat   11100
gtctagcgac tctatccacg gagtgactaa ttcgtaacca ttgacagtct ggttcaaatg  11160
```

```
agtatatatg aaatctaact aaattttgaa gtaaaaatta ttaaaaggat ctaggtgaag    11220 atccttttg ataatctcat gaccaaaatc ccttaacgtg agttttcgtt ccactgagcg    11280 tcagacccg tagaaaagat aattttccta gatccacttc taggaaaaac tattagagta    11340
ctggttttag ggaattgcac tcaaaagcaa ggtgactcgc agtctggggc atcttttcta    11400
caaaggatct tcttgagatc ctttttttct gcgcgtaatc tgctgcttgc aaacaaaaaa    11460
accaccgcta ccagcggtgg tttgtttgcc ggatcaagag gtttcctaga agaactctag    11520 gaaaaaaga cgcgcattag acgacgaacg tttgttttt tggtggcgat ggtcgccacc    11580
aaacaaacgg cctagttctc ctaccaactc tttttccgaa ggtaactggc ttcagcagag    11640
cgcagatacc aaatactgtc cttctagtgt agccgtagtt aggccaccac ttcaagaact    11700
gatggttgag aaaaaggctt ccattgaccg aagtcgtctc gcgtctatgg tttatgacag    11760
gaagatcaca tcggcatcaa tccggtggtg aagttcttga ctgtagcacc gcctacatac    11820
ctcgctctgc taatcctgtt accagtggct gctgccagtg gcgataagtc gtgtcttacc    11880
gggttggact caagacgata gacatcgtgg cggatgtatg gagcgagacg attaggacaa    11940
tggtcaccga cgacggtcac cgctattcag cacagaatgg cccaacctga gttctgctat    12000
gttaccggat aaggcgcagc ggtcgggctg aacgggggt tcgtgcacac agcccagctt    12060
ggagcgaacg acctacaccg aactgagata cctacagcgt caatggccta ttccgcgtcg    12120
ccagcccgac ttgcccccca agcacgtgtg tcggtcgaa cctcgcttgc tggatgtggc    12180
ttgactctat ggatgtcgca gagctatgag aaagcgccac gcttcccgaa gggagaaagg    12240
cggacaggta tccggtaagc ggcagggtcg gaacaggaga gcgcacgagg gagcttccag    12300
ctcgatactc tttcgcggtg cgaagggctt ccctctttcc gcctgtccat aggccattcg    12360
ccgtcccagc cttgtcctct cgcgtgctcc ctcgaaggtc ggggaaacgc ctggtatctt    12420
tatagtcctg tcgggtttcg ccacctctga cttgagcgtc gattttgtg atgctcgtca    12480 gggggcgga gcctatggaa ccccttgcg gaccatagaa atatcaggac agcccaaagc    12540
ggtggagact gaactcgcag ctaaaaacac tacgagcagt cccccgcct cggatacctt    12600 aaacgccagc aacgcggcct ttttacggtt cctggccttt tgctggcctt ttgctcacat    12660
gttctttcct gcgttatccc ctgattctgt ggataaccgt tttgcggtcg ttgcgccgga    12720
aaaatgccaa ggaccggaaa acgaccggaa acgagtgta caagaaagga cgcaataggg    12780
gactaagaca cctattggca attaccgcct ttgagtgagc tgataccgct cgccgcagcc    12840
gaacgaccga gcgcagcgag tcagtgagcg aggaagcgga agagcgccca atacgcaaac    12900
taatggcgga aactcactcg actatggcga gcggcgtcgg cttgctggct cgcgtcgctc    12960
agtcactcgc tccttcgcct tctcgcgggt tatgcgtttg cgcctctccc cgcgcgttgg    13020
ccgattcatt aatgcagctg gcacgacagg tttcccgact ggaaagcggg cagtgagcgc    13080
aacgcaatta atgtgagtta gcggagaggg gcgcgcaacc ggctaagtaa ttacgtcgac    13140
cgtgctgtcc aaagggctga cctttcgccc gtcactcgcg ttgcgttaat tacactcaat    13200
gctcactcat taggcaccccc aggctttaca ctttatgctt ccggctcgta tgttgtgtgg    13260
aattgtgagc ggataacaat ttcacacagg aaacagctat cgagtgagta atccgtgggg    13320
tccgaaatgt gaaatacgaa ggccgagcat acaacacacc ttaacactcg cctattgtta    13380
aagtgtgtcc tttgtcgata gaccatgatt acgccaagct tgcatgcctg caggtcgact    13440
cccttatgaa ccaaggaata gcagatgagt tagtattgat tgatgtaaat aagaataagg    13500
```

```
ctggtactaa tgcggttcga acgtacggac gtccagctga gggaatactt ggttccttat   13560
cgtctactca atcataacta actacattta ttcttattcc cagagggcga tgtgatggat   13620
ttaaatcacg gaaaagtatt cgcgccgaag ccgatgaata tttggtttgg agattatcaa   13680
gattgccaag acgccgattt gtctcccgct acactaccta aatttagtgc cttttcataa   13740
gcgcggcttc ggctacttat aaaccaaacc tctaatagtt ctaacggttc tgcggctaaa   13800
ggtggtgatt tgtgcagggg ctaaccaaaa gccgggagaa acaagactgg atcttgttga   13860
caaaaatatt aatatcttca aaacgattgt cgattctgtg ccaccactaa acacgtcccc   13920
gattggtttt cggccctctt tgttctgacc tagaacaact gtttttataa ttatagaagt   13980
tttgctaaca gctaagacac atgaaatccg gatttgatgg cgtttttctt gtggcaacga   14040
acccagtgga tattttaacg tatgctactt ggaaatttag cgggttaccg aaagagcggg   14100
tactttaggc ctaaactacc gcaaaaagaa caccgttgct tgggtcacct ataaaattgc   14160
atacgatgaa cctttaaatc gcccaatggc tttctcgccc tgcggccgcc ttgctaagtg   14220
aatattttca agtggctccg accaatgtac atgcgtatat tattggcgag catgggggata   14280 cagagctgcc tgtttggagc acgccggcgg aacgattcac ttataaaagt tcaccgaggc   14340
tggttacatg tacgcatata ataaccgctc gtaccectat gtctcgacgg acaaacctcg   14400
catgcggaaa ttggaagcat tccagttgag caaatattga tgcaaaacga taactataga   14460
aaagaggatt tagacaatat ctttgttaat gttcgtgatg gtacgccttt aaccttcgta   14520
aggtcaactc gtttataact acgttttgct attgatatct tttctcctaa atctgttata   14580
gaaacaatta caagcactac cggcatatca aatcattgag aaaaaagggg caacgtatta   14640
cggcattgca atgggattag tccgtatcac tcgtgctatt ttgcacaatg aaaatgccat   14700
gccgtatagt ttagtaactc ttttttcccc gttgcataat gccgtaacgt taccctaatc   14760
aggcatagtg agcacgataa aacgtgttac ttttacggta cttaaccgtt tctgctcatt   14820
tggacggcca atatggcgaa cgaaatgttt atattggcgt gcctgccatt atcaaccgaa   14880
acggtattcg tgaagtgatg gaattggcaa agacgagtaa acctgccggt tataccgctt   14940
gctttacaaa tataaccgca cggacggtaa tagttggctt tgccataagc acttcactac   15000
gaattgacgc tgcaggcatg cacttaactg cgacgtccgt acgt                    15044
```

SPORULATION-DEFICIENT THERMOPHILIC MICROORGANISMS FOR THE PRODUCTION OF ETHANOL

CROSS-REFERENCE TO RELATED APPLICATIONS

This application is a continuation of U.S. application Ser. No. 13/127,927, filed May 13, 2011; which is the National Stage of International Application Number PCT/GB2009/051487, filed Nov. 5, 2009, each of which is hereby incorporated by reference herein in its entirety, including any figures, tables, nucleic acid sequences, amino acid sequences, and drawings.

FIELD OF THE INVENTION

This invention relates to the production of microorganisms suitable for the production of ethanol. In particular, the invention relates to the modification of microorganisms to prevent sporulation.

BACKGROUND TO THE INVENTION

Sporulation is a multi-stage developmental process that is responsible for the conversion of a growing cell into a dormant cell type, known as a spore or endospore. Spores are adapted for dispersal and survival for an extended period of time in unfavourable conditions and form part of the life cycle of many plants, algae and bacteria, such as the *Bacillus* species.

The primary regulator for entry into sporulation is the DNA-binding protein Spo0A (stage 0 sporulation protein A), which is a member of the response regulator family of transcription factors. Numerous other genes, including genes which encode five histidine autokinases (KinA, KinB, KinC, KinD and KinE) and two response proteins (Spo0B and Spo0F), are also involved in the control of the initiation of sporulation (Molle et al.; Mol. Microbiol.; 2003, 50(5): 1683-1701). The activity of Spo0A is governed by a multi-component phosphorelay, which recognises and integrates environmental signals to initiate sporulation (Trach K A, et al; Mol. Microbiol. 1993; 8(1):69-79). Upon phosphorylation of its regulatory N-terminal domain, Spo0A-P binds to a DNA sequence element known as the "0A-box" which activates genes involved in sporulation. Deletion of the C-terminal domain of Spo0A, which is inactive until the N-terminus has been phosphorylated, has been shown to result in a sporulation-negative phenotype (Rowe-Magnus D A, et al; J. Bacteriol.; 2000; 182(15):4352-4355).

Spo0A has also been found to influence, directly or indirectly, the activation or repression of expression of over 500 genes in *B. subtilis*, and therefore indirectly mediates the global pattern of gene transcription via regulatory genes under its control (Molle et al.; Mol. Microbiol.; 2003, 50(5):1683-1701).

Sporulation is subject to catabolite repression, whereby the presence of glucose or other readily metabolized carbon sources inhibits sporulation by wild-type cells. In particular, glucose is known to repress the transcription of spo0A and spo0F (Myseliwiec, T H et al; J. Bacteriol.; 1991; 173(6): 1911-1919).

In a commercial fermentation process spores are undesirable for two main reasons:
1. Sporulation pauses active metabolism by an organism resulting in a reduction or cessation of the formation of a desired metabolic product; and
2. Sporulating microorganisms are more difficult to handle and control containment, therefore it is desirable to avoid the survival of commercial process microorganisms for environmental reasons, including health and safety, and also to prevent the uncontrolled release of the commercial strain.

The general process by which bacteria metabolise suitable substrates is glycolysis, which is a sequence of reactions that converts glucose into pyruvate with the generation of ATP. The fate of pyruvate in the generation of metabolic energy varies depending on the microorganism and the environmental conditions. The four principal reactions of pyruvate are illustrated in FIG. 5.

First, under aerobic conditions, many microorganisms will generate energy using the citric acid cycle and the conversion of pyruvate into acetyl coenzyme A, catalysed by pyruvate dehydrogenase (PDH).

Second, under anaerobic conditions, certain ethanologenic organisms can carry out alcoholic fermentation by the decarboxylation of pyruvate into acetaldehyde, catalysed by pyruvate decarboxylase (PDC) and the subsequent reduction of acetaldehyde into ethanol by NADH, catalysed by alcohol dehydrogenase (ADH).

A third reaction, which also occurs in anaerobic conditions, is the conversion of pyruvate to acetyl CoA, catalysed by pyruvate formate lyase (PFL). Acetyl CoA is subsequently converted into acetaldehyde by the enzyme acetaldehyde dehydrogenase (AcDH) and ethanol is produced by the reduction of acetaldehyde catalysed by ADH.

A fourth process is the conversion of pyruvate into lactate which occurs through catalysis by lactate dehydrogenase (LDH).

There has been much interest in using microorganisms for the production of ethanol using either microorganisms that undergo anaerobic fermentation naturally or through the use of recombinant microorganisms which incorporate the pyruvate decarboxylase and alcohol dehydrogenase genes.

WO2008/038019 discloses microorganisms which comprise modifications to inactivate the native LDH and PFL genes and up-regulate the PDC, PDH and ADH genes in order to promote the formation of ethanol.

There is a need for further improvements to the production of ethanol from microorganisms.

SUMMARY OF THE INVENTION

The present invention is based upon the surprising finding that inhibition of the spo0A gene in spore-forming thermophilic microorganisms results in increased ethanol tolerance of the microorganism, and also increased metabolism, which results in an increase in the rate of production of metabolic end-products such as ethanol.

According to a first aspect of the present invention, a thermophilic microorganism comprises a modification that decreases sporulation compared with wild-type, wherein a first modification inactivates the native spo0A gene.

The microorganism may be further modified to permit increased production of ethanol via inactivation of the native lactate dehydrogenase and, optionally, pyruvate formate lyase genes. Further modification can be made to upregulate the native pyruvate dehydrogenase gene or introducing an active pyruvate decarboxylase gene.

The microorganism may be further modified to permit increased production of ethanol from starch by increasing amylase gene expression.

The microorganism of the invention shows increased ethanol production and increased ethanol tolerance compared to wild-type.

According to a second aspect of the present invention, a method of producing ethanol comprises culturing a microorganism according to the definition provided above in suitable conditions in the presence of a C3, C5 or C6 sugar, or an oligomer thereof.

DESCRIPTION OF THE DRAWINGS

The present invention is described with reference to the accompanying figures, wherein:

FIG. 1 is the Spo0A nucleotide sequence (SEQ ID No.1);
FIG. 2 is the Spo0A amino acid sequence (SEQ ID No.2)

DETAILED DESCRIPTION OF THE INVENTION

Figure 3:
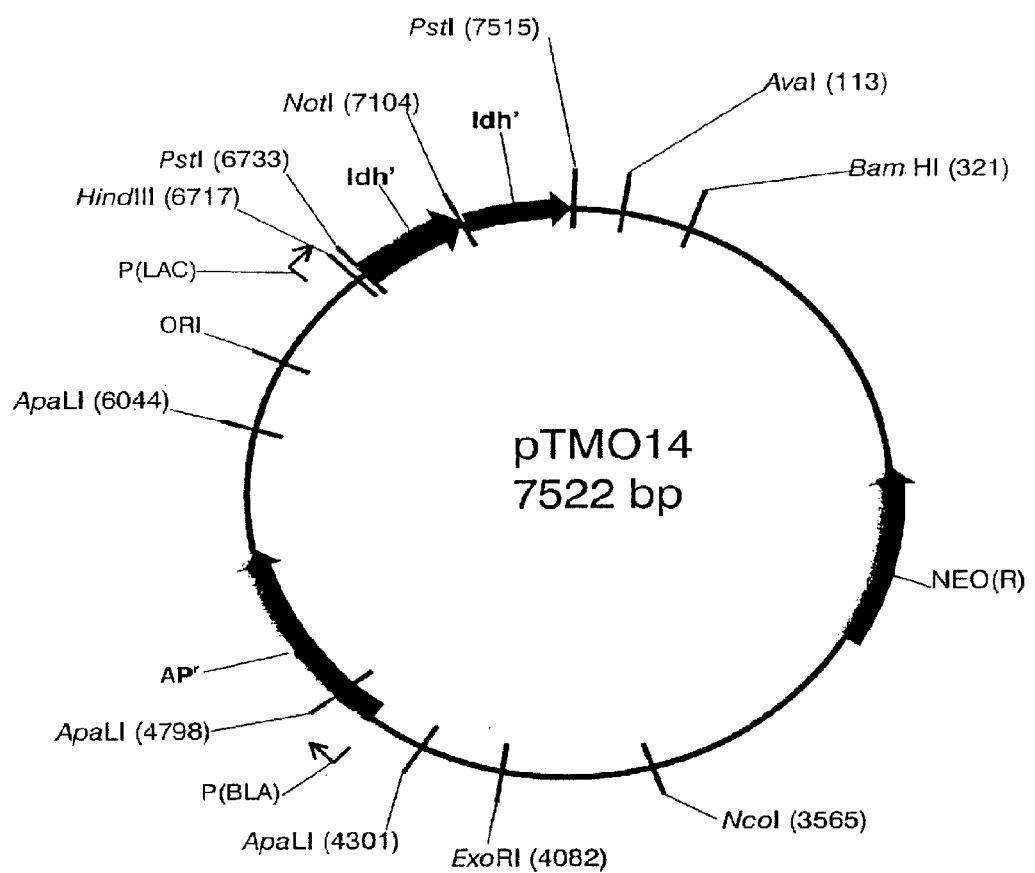
FIG. 3 illustrates the plasmid pTM014 (SEQ ID No.4)

The present invention relates to the modification of a thermophilic microorganism to prevent sporulation.

The invention is based upon the surprising finding that inhibition of sporulation is associated with increased ethanol tolerance, enabling larger yields of ethanol to be produced by microorganisms in batch fermentation processes. Non-sporulating microorganisms also have process advantages since they are easier to handle and control than spore-formers.

Furthermore, due to an increase in metabolism, it has been found that fermentation proceeds to completion at a faster rate when sporulation is prevented.

Sporulation can be prevented by modifying the microorganism to inactivate the native spo0A gene, preferably by deleting at least a portion of the spo0A gene or by targeted disruption of the gene. Preferably, as a result of the modification the microorganism is entirely sporulation-deficient.

The coding sequence of the spo0A gene (SEQ ID No.1) is shown in FIG. 1. The amino acid sequence of the polypeptide encoded by the spo0A gene (SEQ ID No.2) is shown in FIG. 2. Using this coding sequence, it is possible for the skilled person to target spo0A to achieve inactivation of the gene through different mechanisms. It is preferred if the spo0A gene is inactivated by the deletion of the gene sequence, or a portion thereof, preferably the C-terminal domain.

Methods to inactivate the gene will be apparent to the skilled person, based on the knowledge of the gene sequence, as disclosed herein The gene sequence may be deleted or inactivated by insertion of additional DNA to the disrupt gene expression.

Methods of targeted gene disruption are well known in the art and include, for example, the integration of temperature-sensitive plasmids into the target gene on the chromosome. Integration of a plasmid may delete the target gene entirely, or may replace the complete gene with a portion of the gene that is non-functional. This can be achieved by isolating a sequence that includes the gene of interest, excising a portion of the gene, amplifying the remaining fragments, cloning these fragments into a temperature-sensitive plasmid and then transforming target microorganisms with the plasmid. The present invention is not limited to a specific method of inactivating the spo0A gene, however a detailed description of a suitable technique using the plasmid pTMO31 is provided in the 'Example' section.

The microorganism may be any thermophilic microorganism, but it is preferred if the microorganism is of the *Bacillus* species. In particular, it is preferred if the microorganism is a wild-type microorganism of the *Geobacillus* species, in particular *Geobacillus thermoglucosidasius*.

In a preferred embodiment, the microorganisms selected for modification are said to be "wild-type", i.e. they do not comprise any further laboratory-produced mutations in addition to the mutations described herein. The microorganisms may be isolated from environmental samples expected to contain thermophiles. Isolated wild-type microorganisms will have the ability to sporulate. Furthermore, isolated wild-type microorganisms will have the ability to produce ethanol from pyruvate but, unmodified, lactate is likely to be the major fermentation product. The isolates are selected for their ability to grow on hexose and/or pentose sugars, and oligomers thereof, at thermophilic temperatures.

It is preferable that the microorganism of the invention has certain desirable characteristics which permit the microorganism to be used in a fermentation process. The microorganism should preferably have no restriction system, thereby avoiding the need for in vivo methylation. In addition, the microorganism should be stable to at least 3% w/v ethanol, preferably 5-10% w/v ethanol, and most preferably up to 20% w/v ethanol. The microorganisms should have the ability to utilise $C_3$, $C_5$ and $C_6$ sugars (or their oligomers) as a substrate, including cellulose, cellobiose, hemicellulose, starch and xylan. It is preferable if the microorganism is transformable at a high frequency. Furthermore, the microorganism should have a growth rate in continuous culture to support dilution rates of 0.3 $h^{-1}$ and above.

The microorganism will be a thermophile and will grow in the temperature range of 40° C.-85° C. Preferably, the microorganism will grow within the temperature range 50° C.-70° C. In addition, it is desirable that the microorganism grows in conditions of pH 8 or below, in particular pH 4.5-pH 6.9.

Preferred microorganisms of the invention are identified herein as TM443 and TM444, each of which has been deposited at NCIMB Ltd, Ferguson Building, Craibstone Estate, Bucksburn, Aberdeen AB21 9YA with NCIMB Accession Nos. 41591 and 41588 respectively.

The thermophilic microorganism of the invention may be further modified to disrupt the expression of the lactate dehydrogenase gene (LDH).

Inactivating the lactate dehydrogenase gene helps to prevent the breakdown of pyruvate into lactate, and therefore promotes (under appropriate conditions) the breakdown of pyruvate into ethanol using pyruvate decarboxylase and alcohol dehydrogenase. It is preferable for the lactate dehydrogenase gene to be disrupted by a deletion within, or of, the gene.

The nucleic acid sequence for lactate dehydrogenase is now known. Using this sequence, it is possible for the skilled person to target the lactate dehydrogenase gene to achieve inactivation of the gene through different mechanisms. It is possible to inactivate the lactate dehydrogenase gene by the insertion of a transposon. However, it is preferred if the lactate dehydrogenase gene is inactivated by the deletion of the gene sequence or a portion of the gene sequence. Deletion is preferred, as this avoids the difficulty of reactivation of the gene sequence which is often experienced when transposon inactivation is used. In a preferred embodiment, the lactate dehydrogenase gene is inactivated by the integration of a temperature-sensitive plasmid, which achieves natural homologous recombination or integration between the plasmid and the microorganism's chromosome. Preferably, the plasmid is pTM014 (SEQ ID No.4), which is illustrated in FIG. 3. Chromosomal integrants can be selected for on the basis of their resistance to antibacterial agents. The integration into the lactate dehydrogenase gene may occur by a single cross-over recombination event or by a double (or more) cross-over recombination event.

The microorganism may also be modified to up-regulate the pyruvate dehydrogenase gene (PDH). Up-regulating the pyruvate dehydrogenase gene promotes the conversion of pyruvate into acetyl CoA, which can then be used, under appropriate conditions, to produce acetaldehyde and eventually ethanol using acetaldehyde dehydrogenase. A further advantage of up-regulating PDH is that pyruvate levels, which have an inhibitory effect on glucose uptake and glycolysis, are reduced. This further promotes ethanol production. PDH is a large enzyme complex, containing three units—E1: pyruvate decarboxylase (EC 1.2.4.1, not EC 4.1.1.1), E2: dihydrolipoamide transacetylase, and E3: dihydrolipoamide dehydrogenase. The complex requires several cofactors, including NAD, FAD, coenzyme A lipoic acid and thiamine pyrophosphate (TPP). Four genes code for the complex, as the E1 unit is a heterodimer of α and β subunits, and are often described as pdhA, pdhB, pdhC and pdhD (E1α, E1, E2β and E3 respectively). The E1 unit of PDH requires TPP in the same way that PDC (EC 4.1.1.1) requires TPP and catalyses a similar decarboxylation reaction, but in the presence of coenzyme A and lipoic acid—carried by other enzyme units—the product is acetyl CoA rather than acetaldehyde. However, PDC activity of the E1 unit has been measured when it has not been complexed with other units in PDH (Lessard & Perham; *The Journal of Biological Chemistry*; 1994, 269; 14, 10378-10383; Tomar et al; *Applied Microbiology and Biotechnology*; 2003, 62, 76-82; Frank et al; *Science*; 2004, 306; October 29, 872-876, supplementary data). Accordingly, PDC activity of EC 1.2.4.1 may be enhanced by the up-regulation of PDH so that acetaldehyde is produced over and above acetyl CoA. Enhanced PDH activity is also sought to remove the pyruvate bottleneck observed in LDH inactivated strains to allow more ethanol to be produced with less acetate and formate as side products.

To this end, the PDH genes and surrounding sequence were isolated using standard "genome walking" techniques. Approximately 8.8 kb of DNA was isolated, sequenced and found to contain the following genes shown in FIG. 4 and Table 1.

TABLE 1

| Gene | Position (bp) | Proposed Function | Frame (aa's at 5' and 3') | Size (aa) |
| --- | --- | --- | --- | --- |
| pdf2 | 746-192 | Peptide deformylase | −3 (MIT-IER) | 184 |
| orf2 | 868-1497 | Unknown - Hypothetical protein | +1 (MQR-IWK) | 209 |
| pdhA(α) | 1875-2984 | α - subunit of pyruvate hydrogenase | +3 (MGA-ESK) | 369 |
| pdhA(β) | 3003-3965 | β - subunit of pyruvate dehydrogenase | +3 (MIQ-INF) | 320 |
| pdhB | 4058-5368 | Dihydrolipoamide transacetylase | +2 (VAF-MEA) | 436 |
| lpd | 5373-6785 | Lipoamide dehydrogenase | +3 (MVV-ISK) | 470 |
| orf7 | 7432-6833 | Unknown - Hypothetical protein | −1 (MNK-CTE) | 199 |
| orf8 | 7964-8647 | Transposase | +2 (MDL-SPP) | 227 |

Figure 4:
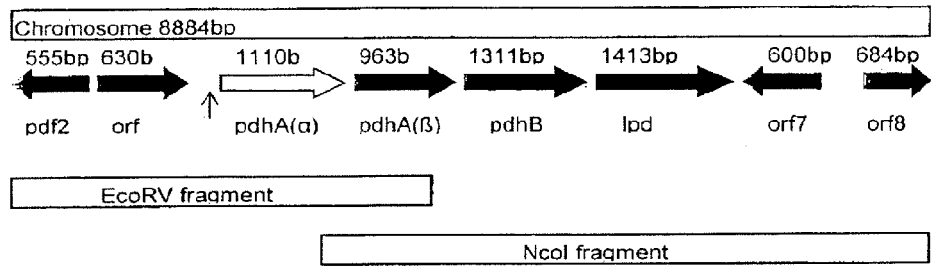
FIG. 4 illustrates the hypothetical promoter regions and genes of the PDH complex.
Figure 5:
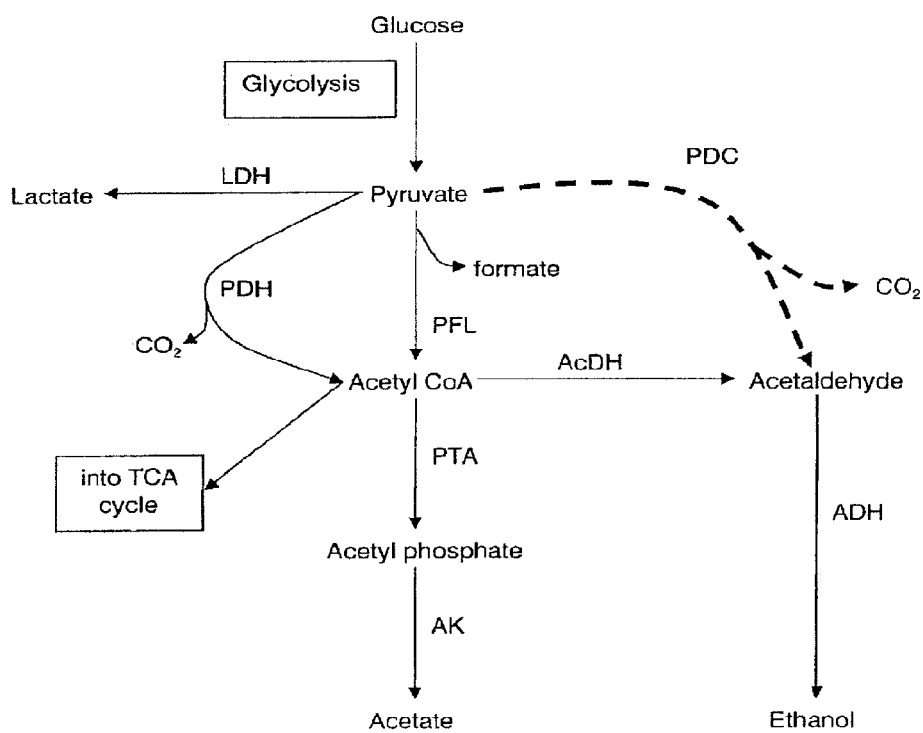
FIG. 5 illustrates the four principal reactions of pyruvate.

The hypothetical promoter regions are shown in FIG. 4 (arrow)—one upstream from the start of pdhA and a possible second promoter ahead of pdhB. A previous example of a secondary promoter in the PDH cluster was reported for *Bacillus subtilis* (Gao et al; *Journal of Bacteriology*, 2002, 184:10, 2780-2788), but most described PDH gene clusters have just one promoter upstream of the cluster (Neveling et al; *Biochimica Acta*; 1998 1385. 367-372). The upregulation can be carried out using techniques known in the art. In particular, upregulation can be carried out by introducing a suitable promoter or enhancer sequence upstream of the PDH complex.

The enzyme complex is known to work under both aerobic and anaerobic conditions (Carlsson et al; *Infection and Immunity;* 1985, 49(3):674-678) but it is generally considered to be an aerobic enzyme (Ch 15; *Principles of Biochemistry*; Lehninger, Nelson & Cox; 2$^{nd}$ Ed, Worth Publishers, New York, 1993, p 447) with pyruvate formate lyase (PFL) its anaerobic counterpart. Both enzymes convert pyruvate, formed in glycolysis, to acetyl CoA to feed into the TCA cycle but the cycle only works completely under aerobic conditions. However, as it is desirable to use anaerobic conditions, promoters that operate in anaerobic conditions are preferred for use in the invention. Thus promoters for enzymes believed to work under anaerobic conditions—examples being the LDH promoter (P_ldh from *G. stearothermophilus* NCA1503), the PFL promoters (P_pfl from *B. cereus* ATCC14579, and *G. thermoglucosidasius* NCIMB11955) and ferredoxin promoters (P_ferrA from *G. stearothermophilus* DSM13240)—can be used, as in PCT/GB2007/03699 which is incorporated herein by reference.

In a preferred embodiment, a further modification is introduced to enhance the PDC activity, thereby promoting the conversion of pyruvate to acetaldehyde. This can be carried out by inactivating E2 (EC 2.3.1.12). Inactivation can be carried out in a manner similar to the inactivation of LDH, but with the E2 gene as the target for disruption.

In a further embodiment, a microorganism of the invention comprises a modification to inactivate the pyruvate formate lyase gene, thereby preventing/reducing the conversion of pyruvate to acetyl CoA and formate. Pyruvate formate lyase (PFL) is the "anaerobic counterpart" to pyruvate dehydrogenase (PDH) and converts pyruvate to acetyl CoA and formate (see FIG. 6). While acetyl CoA can be converted to ethanol via acetaldehyde dehydrogenase (AcHD), formate is an undesired side-product which has the potential to inhibit growth in ethanolgenic organisms.

PFL was chosen as a target for knockout in order to promote the metabolic flux towards ethanol production and to improve the redox balance of the remaining pathway to ethanol synthesis. An additional advantage of this work was the elimination of formate production. PFL activity can be inactivated via transposon insertion, gene deletion or partial gene deletion to produce a mutant which does not rely on antibiotic selection for the continuation of the altered phenotype. However, it is preferred if the pyruvate formate lyase gene is inactivated by the deletion of the gene sequence or a portion of the gene sequence. Deletion is preferred, as this avoids the difficulty of reactivation of the gene sequence which is often experienced when transposon inactivation is used. In this embodiment, it is preferred that the microorganism comprises both the lactate dehydrogenase inactivation and the up-regulation of the pyruvate dehydrogenase, so that, under anaerobic conditions, ethanol production is increased.

In a further preferred embodiment, the microorganism also comprises up-regulated pyruvate decarboxylase and/or alcohol dehydrogenase genes. The expression of these genes results in the production of enzymes which redirect the metabolism so that ethanol is the primary fermentation product. If the PDC gene is EC4.1.1.1, the gene will be heterologous and can be inserted in an expression cassette, as will be appreciated by the skilled person. If the PDC gene is EC1.2.4.1, it can be the homologous gene that is upregulated. The ADH gene may be heterologous or homologous. If the native gene is to be utilised, it may be upregulated by methods known in the art. Preferably, both PDC and ADH are expressed in the microorganism. The genes may be obtained from microorganisms that typically undergo anaerobic fermentation, including *Zymomonas* species, including *Zymomonas mobilis*.

Methods of the preparation and incorporation of a gene into microorganisms are known, for example in Ingram et al, Biotech & BioEng, 198; 58 (2 and 3): 204-214 and U.S. Pat. No. 5,916,787, the content of each being incorporated herein by reference. The gene may be introduced in a plasmid or integrated into the chromosome, as will be appreciated by the skilled person.

The thermophilic microorganism of the invention may be further modified to increase amylase gene expression compared to wild-type. Such modification is described in detail in WO2009/022158, the content of which is incorporated herein. This enables the microorganism to hydrolyse starch into glucose monomer units which can then be utilised as glycolytic substrates for the formation of pyruvate and subsequently ethanol. This modification therefore enables the increased production of ethanol from cheap, abundant, un-refined plant material.

Methods of increasing amylase expression and enzyme activity include the use of strong up-stream promoters to regulate transcription of the gene, incorporation of additional amylase genes that are expressed at a higher frequency than the native amylase gene, or the expression of a more active amylase gene. The term "strong promoter" is defined herein as a promoter that expresses the corresponding protein to a level greater than 0.5% of the soluble protein in a cell.

In a preferred embodiment, a heterologous amylase gene encodes α-amylase (α-1,4-glucan-4-glucanohydrolase, EC 3.2.1.1). It is preferred that the amylase gene is derived from the *Geobacillus* species, in particular *Geobacillus stearothermophilus*.

The coding sequence of the α-amylase gene has been elucidated and the techniques enabling isolation and amplification of the gene are well known in the art. In order to enable the microorganism of the invention to exhibit increased amylase expression compared to wild-type, it is preferred that the amylase gene is placed under the control of a strong promoter, which operates in low-aeration or anaerobic conditions that favour ethanol production by thermophilic microorganisms. The promoter is preferably an ldh promoter and may be autologous, but is preferably heterologous, and is most preferably derived from the same species as the amylase gene. Examples of suitable promoters include, but are not limited to, P_ldh from *G. stearothermophilus* NCA1503, P_ferrA from *G. stearothermophilus* DSM13240 and P_pfl from *B. cereus* ATCC14579.

In another embodiment of the invention, a series of different strong promoters are placed upstream of the amylase gene in order to further enhance expression. Examples of suitable strong promoters include, but are not limited to, the glyceraldehyde-3-phosphate promoter (P_GAPDH) and amylase promoter from *G. stearothermophilus* NCA 1503.

The nucleic acid sequence of P_ldh is also known and techniques for cloning and assembling the promoter sequence upstream of the amylase gene are known to the skilled person.

Figure 6:
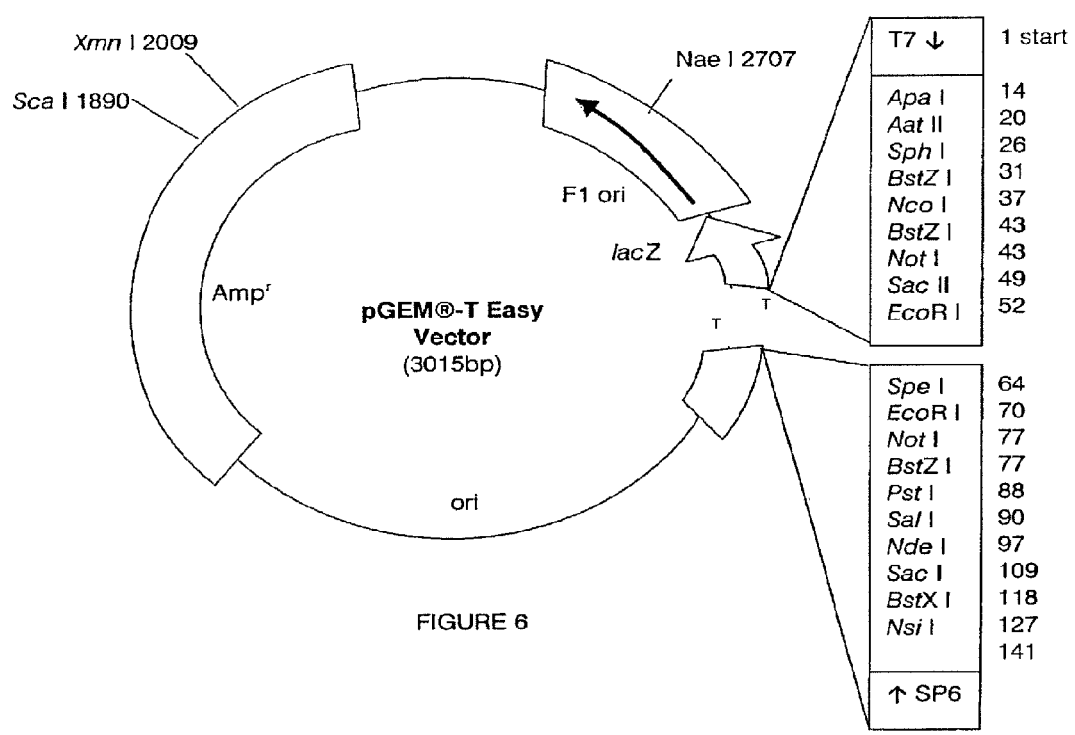
FIG. 6 illustrates the pGEM®-T Easy Vector.
Figure 7:
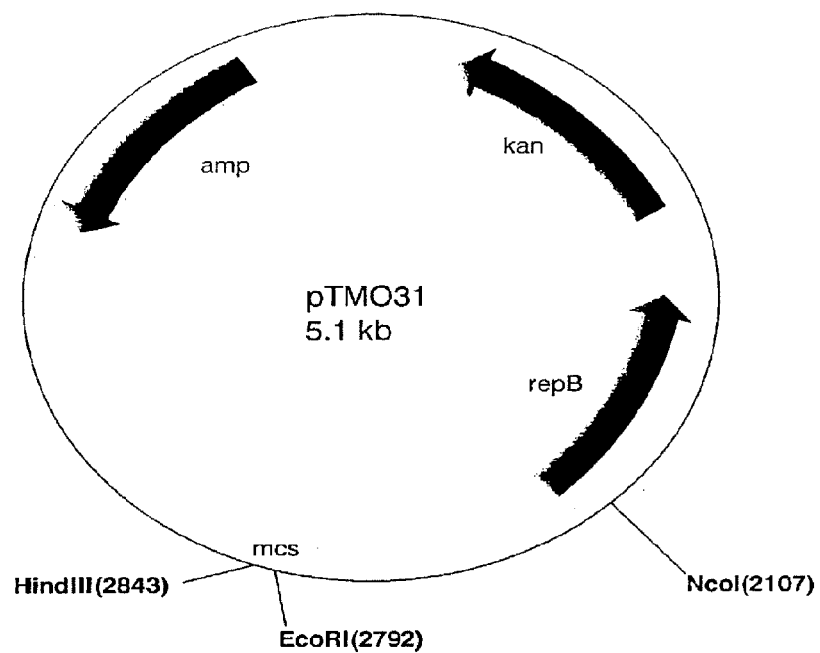
FIG. 7 illustrates the plasmid pTM031 (SEQ ID No.3)

The promoter/amylase sequence can be cloned into a suitable plasmid or expression vector containing multiple restriction sites. There are numerous suitable expression vectors which are commercially available, such as the pGEM®-T Easy Vector (FIG. 6). Restriction enzymes can be used to excise the P_ldh/amylase construct as a specific fragment which can be ligated into the corresponding restriction site in a temperature-sensitive plasmid such as pTMO31 (FIG. 7, SEQ ID No. 3) able to use a pyruvate formate lyase knock-out plasmid. The plasmid construct comprising the amylase gene/ldh promoter can then be electroporated into the microorganism of the invention with subsequent homologous recombination with genomic DNA. Chromosomal integrants can be selected for on the basis of their resistance to antibacterial agents, such as ampicillin or kanamycin. Amylase activity can also be visualised as zones of starch clearing, for example on plate assays. The culture media may preferably comprise at least 1% w/v starch, preferably at least 10% w/v starch, and most preferably at least 20% w/v starch. The starch may be soluble or insoluble (e.g. grain starch).

An embodiment of the present invention will now be described, with reference to the accompanying drawings, in the following example. The present invention is exemplified but not limited, by the example.

EXAMPLE

Figure 8:
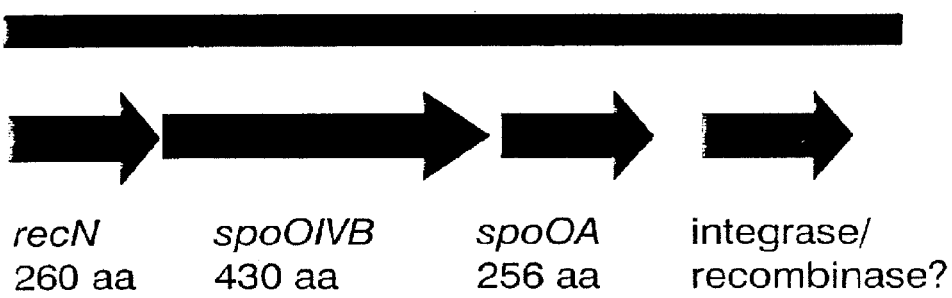
FIG. 8 illustrates schematically the organisation of spo0A and surrounding genes from a 4480 bp sequence read of genomic DNA isolated from *G. thermoglucosidasius*.

Two different Spo0A knock-out constructs were developed to take account of other sporulation genes adjacent to the target spo0A which could be transcriptionally affected upon out-of-frame spo0A disruption, as illustrated in FIG. 8.

Figure 9:
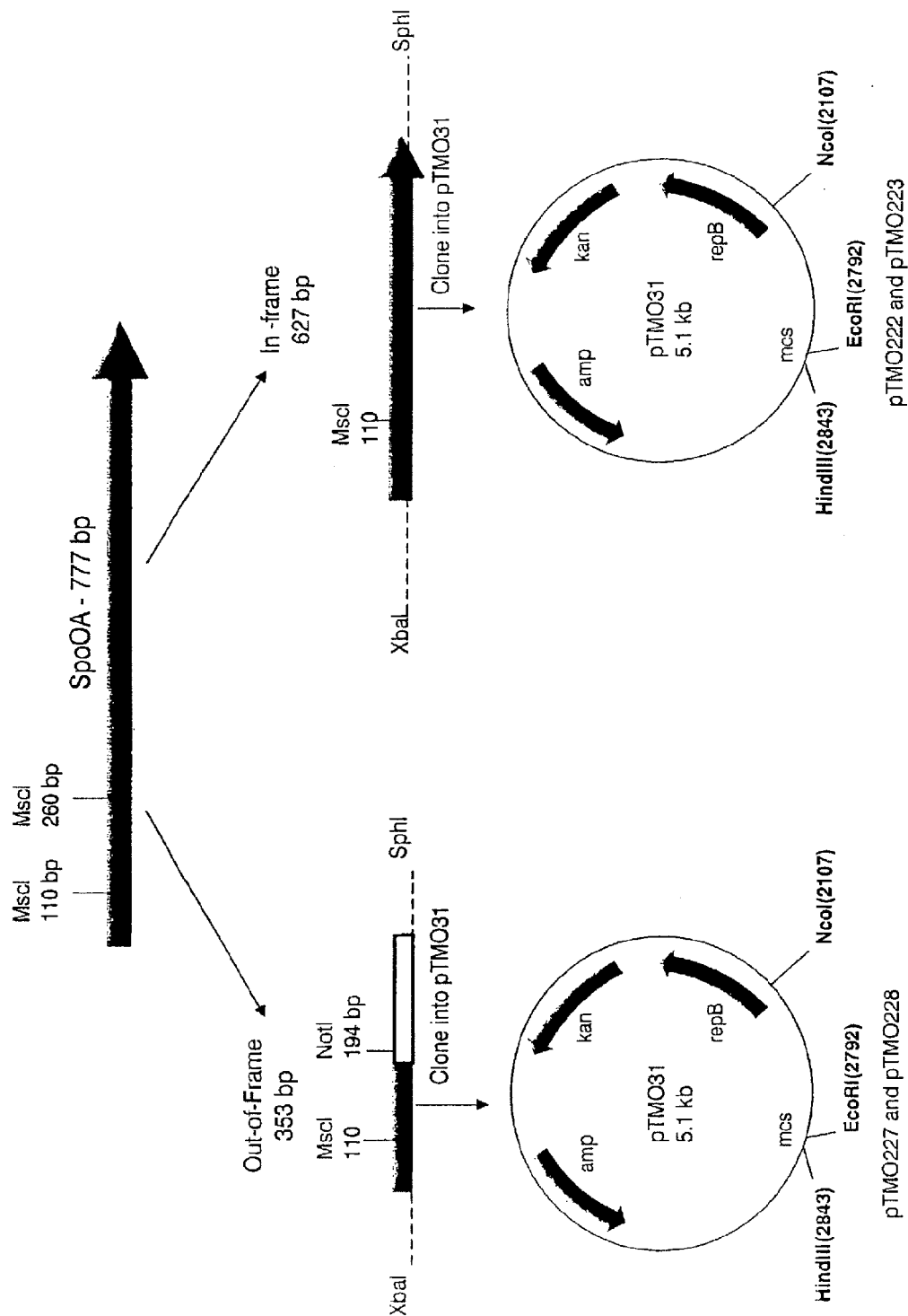
FIG. 9 outlines the two approaches to disrupting the spo0A gene.

Thus an out-of-frame and an in-frame knockout cassette were produced as outlined in FIG. 9. The out-of-frame cassette was generated by the removing of a 429 bp region of the spo0A gene and replacing it with an engineered NotI restriction site to enable hybridisation of primers for PCR amplification of fragments comprising spo0A deletions, while the in-frame cassette was constructed by removing the naturally occurring 150 bp MscI-MscI fragment.

The resulting fragments were cloned into pTM031, which is a 5.1 kb plasmid derived from an EcoRI/SnaBI pUB110 fragment insert into pUC19. The plasmid map of pTM031 is illustrated in FIG. 3 and the nucleic acid sequence of pTM031 corresponds to SEQ ID No.7. Nucleotides 1-239, 2634-2791 and 2848-5082 are derived from pUC19, nucleotides 240-2633 are derived from pUB110 and the remaining nucleotides (2792-2848) correspond to the multiple cloning site (MCS).

The resulting plasmids were then used to transform *Geobacillus* microorganisms which incorporated other modifications as set out below. Methods of transformation, primary integration and stabilisation via selection of double cross-over mutants were employed in a variety of strain backgrounds, as detailed below.

*Geobacillus thermoglucosidasius* Strain Backgrounds

| Strain name | Modification(s) |
|---|---|
| TM89 | ldh$^-$ |
| TM242 | ldh$^-$, pdh_up, pfl$^-$ |
| TM266 | ldh$^-$, pdh_up, P_ldh(Ste), pfl$^-$ |
| TM379 | ldh$^-$, pdh_up, P_pfl(11955), pfl$^-$ |
| TM333 | ldh$^-$, pdh_up, pfl$^-$, P_ldh(NCA)/amyS(DSM22) |

Results

Generation of Spo0A Mutants in TM242

A total of 20 presumptive primary integrants (4 in-frame and 16 out-of-frame) of TM242 (NCIMB Accession No. 41589) were sub-cultured through two rounds of growth in 2TY medium at 60° C. Cells from each of these cultures were plated onto TGP medium and subsequently replicated onto TGP containing kanamycin at a final concentration of 12.5 μg/ml. A total of 13 (5 in-frame, 8 out-of-frame) kanamycin-sensitive strains representing putative double cross-over mutants with a disrupted spo0A gene were identified.

Difco Sporulation Medium (DSM), made according to the following recipe, was used to demonstrated the ability of the mutants to sporulate. Testing was conducted before and after heat treatment to kill vegetative cells.

Difco Sporulation Medium (DSM)

| | Per liter |
|---|---|
| Bacto nutrient broth (Difco) | 8 g |
| 10% (w/v) KCl | 10 ml |
| 1.2% (w/v) MgSO$_4$•7H$_2$O | 10 ml |
| 1M NaOH | ~1.5 ml (pH to 7.6) |

The volume is adjusted to 1 liter with ddH$_2$0 and the pH is adjusted to 7.6. The solution is then autoclaved and allowed to cool to 50° C. The following sterile solutions (and antibiotics if required) are added prior to use:

| | |
|---|---|
| 1M Ca(NO$_3$)$_2$ | 1 ml |
| 0.01M MnCl$_2$ | 1 ml |
| 1 mM FeSO$_4$ | 1 ml |

A dilution series for TM242 and one of its out-of-frame Spo0A-negative offspring, TM443, were plated on TGP both before and after both strains were heat treated at 90° C. for 30 minutes. When not subjected to heat treatment, there was comparable growth between TM242 and TM443 at each dilution. However, after heat treatment there was a clear difference. While TM242 still showed growth at each dilution, albeit less than before heat treatment, there was no growth on the TM443 plate—even in the neat culture patch—indicating that TM242 can sporulate but TM443 cannot. To date, everything that has been done to make these strains sporulate has indicated that they are not capable of doing so.

Figure 10:
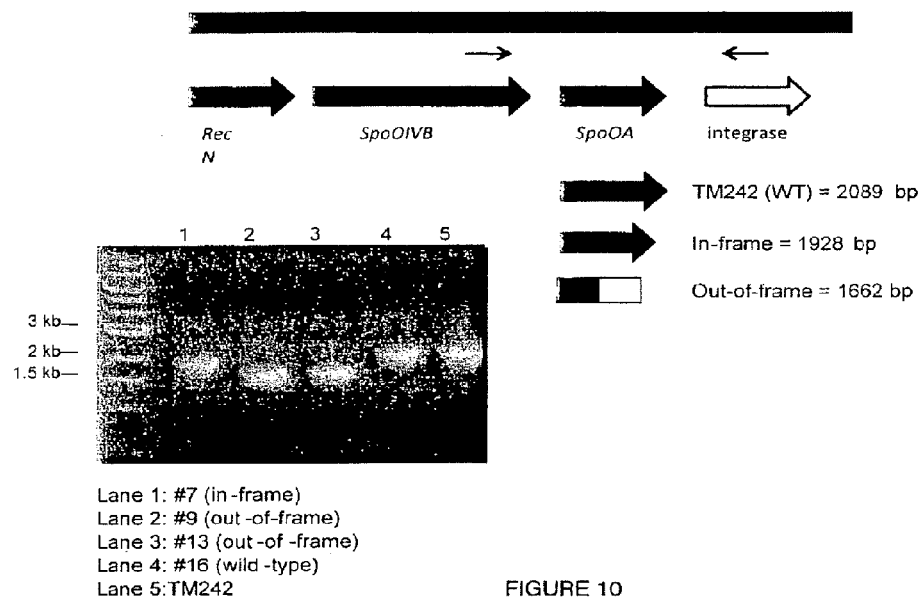
FIG. 10 illustrates the expected PCR product sizes of spo0A knock-out compared with the original spo0A gene.

In addition, genomic DNA was isolated from the TM242 double cross-over mutants and used as templates in PCR reactions together with the primers O/Spo0A1bF and O/Spo0A2R which flank the spo0A region, see FIG. 10. PCR products were generated for each template and analysed by specific restriction enzyme digestion. The DNA fragments generated by these restriction digests are consistent with two of the strains representing out-of-frame mutants of the spo0A gene and one strain representing an in-frame deletion. Southern hybridisation analysis confirmed these results. Therefore, it can be concluded that a) the target spo0A gene has been knocked-out; and b) this has resulted in loss of sporulation in these strains.

Fermentation Characteristics of Spo0A Negative Strains

The improved fermentation characteristics of Spo0A negative strains at lower sugar concentrations were demonstrated using urea salts media (USM) made according to the following recipe:

Urea Salts Media (USM)

| | Final Concentration |
|---|---|
| NaH$_2$PO$_4$•2H$_2$O | 10 mM |
| K$_2$SO$_4$ | 10 mM |
| Citric acid | 2 mM |
| MgSO$_4$•7H$_2$O | 1.25 mM |
| CaCl$^2$•2H$_2$O | 0.02 mM |
| Na$^2$MoO$^4$•2H$_2$O | 1.65 mM |
| Urea | 50 mM |
| ZnSO$_4$•7H$_2$O | 25 μM |
| FeSO$_4$•7H$_2$O | 100 μM |
| MnSO$_4$•H$_2$O | 50 μM |
| CuSO$_4$•5H$_2$O | 5 μM |
| CuSO$_4$•7H$_2$O | 10 μM |
| NiSO$_4$•6H$_2$O | 16.85 μM |
| H$_3$BO$_3$ | 6.5 μM |

The above components were added to deionised water and the following filter-sterilised reagents were added:

| | |
|---|---|
| Biotin | 12.5 μM |
| Yeast extract | 0.5% w/v (after autoclaving) |

As shown in Tables 2A and 2B, it appears that under controlled fermentation conditions (1 L batch, USM with 3% w/v glucose, 1% w/v yeast extract, pH 6.8, 60° C., aeration regime: 1 L/min and 600 rpm until OD>5.0 then 0.2 L/min and 300 rpm) the out-of-frame mutant TM444 is able to consume sugar faster than TM242 and the in-frame mutants TM448 and TM450 perform less well.

TABLE 2A

| Strain | Spo$^-$ | Aeration Switch | | Complete sugar consumption/ hours | Max OD$_{600}$ | Glucose/ mM | Pyruvate/ mM |
|---|---|---|---|---|---|---|---|
| | | Hrs | OD | | | | |
| TM242 | | 2.5 | 5.6 | 7.5 | 9.8 | 0.0 | 1.0 |
| TM443 | ✓o | 2.3 | 5.8 | 6.7 | 8.6 | 0.0 | 0.0 |
| TM444 | ✓o | 2.2 | 5.6 | 5.6 | 9.0 | 0.0 | 0.0 |
| TM448 | ✓i | 3.0 | 5.3 | 9.8 | 7.2 | 0.0 | 1.0 |
| TM450 | ✓i | 3.8 | 5.7 | 9.9 | 8.3 | 0.0 | 3.0 |

TABLE 2A-continued

| Strain | Spo⁻ | Aeration Switch Hrs | OD | Complete sugar consumption/ hours | Max OD$_{600}$ | Glucose/ mM | Pyruvate/ mM |
|---|---|---|---|---|---|---|---|

NB: 'i' denotes in-frame mutant, 'o' denotes out-of-frame mutant

TABLE 2B

| Strain | Lactate/ mM | Formate/ mM | Actate/ mM | Ethanol/ mM | Ethanol yield post aeration switch/gg$^{-1}$ | Overall ethanol yield/ gg$^{-1}$ |
|---|---|---|---|---|---|---|
| TM242 | 10.0 | 0.0 | 13.0 | 314.0 | 0.44 | 0.42 |
| TM443 | 16.0 | 0.0 | 15.0 | 300.0 | 0.44 | 0.40 |
| TM444 | 13.0 | 0.0 | 15.0 | 303.0 | 0.46 | 0.42 |
| TM448 | 6.0 | 0.0 | 21.0 | 243.0 | 0.42 | 0.33 |
| TM450 | 5.0 | 0.0 | 28.0 | 252.0 | 0.43 | 0.35 |

As shown in Table 2B, the ethanol yield post-aeration switch of TM443 is equal to that of the parent strain TM242, whilst for TM444 is slightly improved. More importantly however, as shown in Table 2A, at these lower sugar concentrations (3% w/v glucose) TM443 and TM444 complete sugar consumption significantly faster than TM242. This is an advantageous characteristic in a commercial fermentation process. It is worth noting that in these fermentations, at 3% (w/v) sugar concentrations, TM444 and TM443 are able to utilise sugar more quickly. This is beneficial, as it allows more fermentation batches to be run over time, resulting in significant increases in overall ethanol production.

Figure 11:
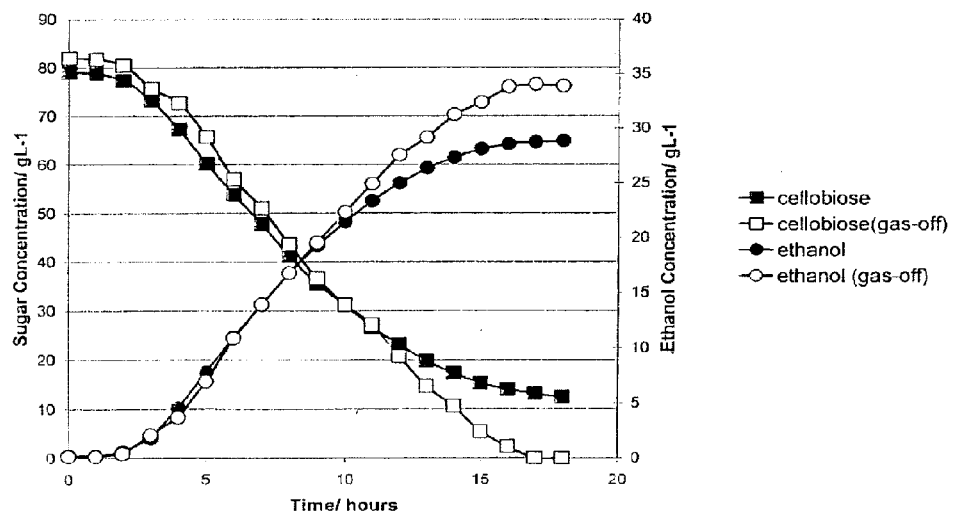
FIG. 11 is a graph showing alterations in the fermentation characteristics of TM242 in media comprising 8% w/v cellobiose and 2% yeast extract when ethanol vapour is partitioned from the fermentation broth ("gas-off") and when it is not partitioned from the broth.

The enhanced ethanol tolerance of TM444 compared to TM242 is illustrated in FIG. 11. It has been found that fermentation of 8% w/v cellobiose by TM242 could proceed to completion only if the ethanol produced during fermentation was partitioned into the vapour phase and remove from the fermentation broth. As shown in FIG. 11, when ethanol vapour was removed from the fermenter during fermentation (i.e. "gas-off") TM242 was able to utilise all of the cellobiose by the end of the fermentation, and the resulting total concentration of ethanol produced was increased, compared with fermentation without the removal of ethanol vapour from the broth. Interestingly, it was not necessary to portion off ethanol vapour in order for the same fermentation media to be fully fermented by TM444. This is because TM444 exhibits improved ethanol tolerance.

Figure 12A:
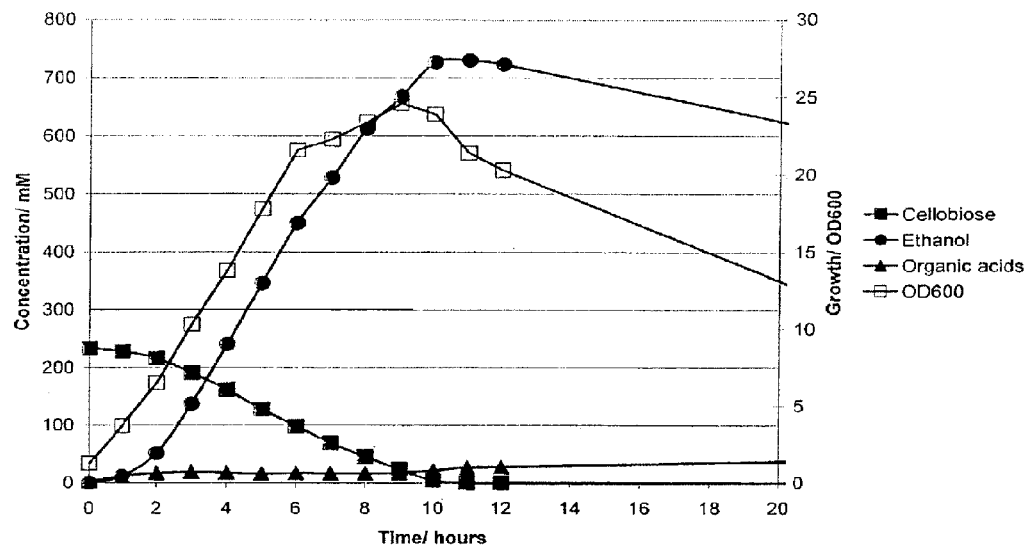
FIG. 12*a* is a graph showing the fermentation characteristics of TM242 in media comprising 8% w/v cellobiose and 2% w/v yeast extract and FIG. 12*b* shows the fermentation characteristics of TM444 in the same media.
Figure 12B:
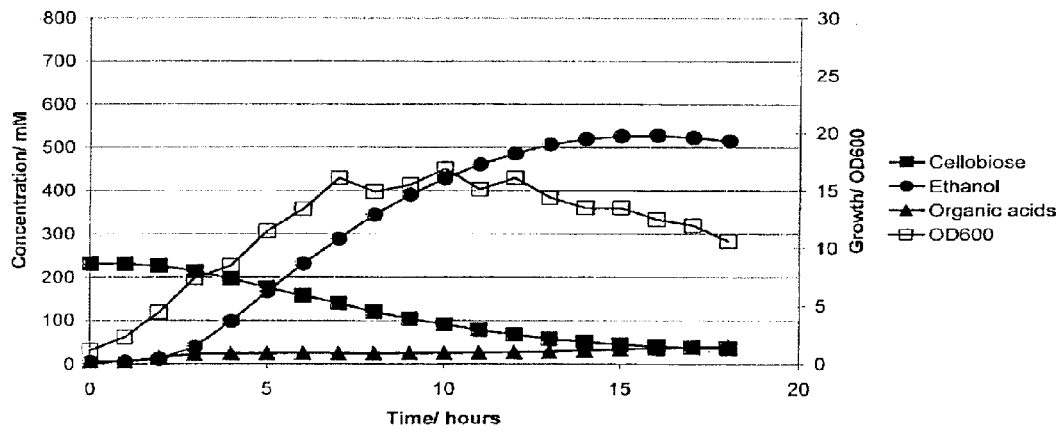

The improved fermentation characteristics of TM444 are further illustrated in FIGS. 12a and 12b, which show the fermentation curves for TM242 and TM444 respectively in media comprising 8% w/v cellobiose and 2% w/v yeast extract. By comparing the two graphs, it can be seen that, at elevated sugar concentrations, TM444 completed sugar consumption in approximately 10 hours, whilst some sugar still remained after 18 hours (i.e. the end of fermentation) when TM242 was used. Furthermore, the ethanol peak for TM242 shown in FIG. 12a is significantly lower than the ethanol peak for TM444 shown in FIG. 12b (527 mM for TM242 compared with 729 mM for TM444).

Therefore, it can be concluded from the data presented in FIGS. 11, 12a and 12b that, at elevated sugar concentrations, the sporulation-deficient mutant strains of the invention exhibit improved ethanol tolerance, an increased rate of sugar consumption and an increase in overall ethanol yield, compared to the parent strain.

Generation of Spo0A Mutants in TM333

In further work, TM333 presumptive primary integrants of the Spo0A gene were sub-cultured through two successive rounds of growth in 2TY broth without antibiotic. Cells from the final round of sub-culturing were serially diluted and grown on TGP medium. Kanamycin-sensitive colonies representing potential double crossovers were identified by replica plating. Through a combination of PCR analysis and testing for sporulation, TM486, an out-of-frame sporulation-deficient derivative of TM333 has been identified as a useful strain for ethanol production. The TM486 strain has been deposited at NCIMB Ltd, Ferguson Building, Craibstone Estate, Bucksburn, Aberdeen AB21 9YA and has the Accession No. NCIMB 41587.

Since this strain comprises the amyS gene present in the parent strain TM333, it provides the combined advantages of increased ethanol tolerance, rapid feedstock consumption and improved ethanol production that are associated with the spo0A mutation, together with the capacity to efficiently metabolise starch-based feedstock due to increased amylase activity.

The content of all of the publications referred to in the description is incorporated herein by reference.

The invention claimed is:

1. An isolated thermophilic microorganism comprising a modification that decreases sporulation compared with wild-type, wherein the modification inactivates the native stage 0 sporulation protein A (spo0A) gene, wherein the microorganism further comprises a modification that inactivates the native lactate dehydrogenase (ldh) gene, wherein the microorganism is a *Geobacillus* species, and wherein the modification of the native spo0A gene increases the microorganism's ethanol tolerance and rate of ethanol production relative to the microorganism without the modification of the spo0A gene.

2. The microorganism according to claim 1, wherein the modification that decreases sporulation comprises the deletion of at least a portion of the spo0A gene.

3. The microorganism according to claim 2, wherein the modification that decreases sporulation further comprises replacing the deleted portion of the spo0A gene with DNA encoding a restriction site.

4. The microorganism according to claim 3, wherein the restriction site is a NotI restriction site.

5. The microorganism according to claim 1, wherein the lactate dehydrogenase gene, or a portion thereof, has been deleted.

6. The microorganism according to claim 1, wherein the microorganism does not comprise an integration element in the lactate dehydrogenase gene.

7. The microorganism according to claim 1, further comprising a modification that inactivates the native pyruvate formate lyase gene.

8. The microorganism according to claim 7, wherein the pyruvate formate lyase gene, or a portion thereof, has been deleted.

9. The microorganism according to claim 1, further comprising a modification that up-regulates the pyruvate dehydrogenase gene.

10. The microorganism according to claim 9, wherein a gene promoter is inserted upstream of the pyruvate dehydrogenase gene, and wherein the promoter operates under anaerobic conditions.

11. The microorganism according to claim 1, further comprising a modification that enhances pyruvate decarboxylase activity.

12. The microorganism according to claim 11, wherein the modification inactivates the dihydrolipoamide transacetylase gene (EC 2.3.1.12).

13. The microorganism according to claim 11, wherein the dihydrolipoamide transacetylase gene, or a portion thereof, is deleted.

14. The microorganism according to claim 1, wherein the microorganism comprises a heterologous pyruvate decarboxylase gene.

15. The microorganism according to claim 1, wherein the microorganism comprises a heterologous alcohol dehydrogenase gene.

16. The microorganism according to claim 1, wherein the microorganism comprises a heterologous amylase gene under the control of a promoter which operates in anaerobic conditions.

17. A method of producing ethanol, comprising culturing the thermophilic microorganism of claim 1 under suitable conditions in the presence of a $C_3$, $C_5$, or $C_6$ sugar, or oligomer thereof.

18. A method of producing ethanol, comprising culturing the thermophilic microorganism of claim 1 in culture media comprising at least 1% w/v starch.

19. The microorganism according to claim 2, wherein the deletion of at least a portion of the spo0A gene is at the carboxy-terminal domain.

* * * * *